US007766907B2

(12) United States Patent
Dando et al.

(10) Patent No.: US 7,766,907 B2
(45) Date of Patent: Aug. 3, 2010

(54) ABLATION CATHETER WITH SENSOR ARRAY AND DISCRIMINATION CIRCUIT TO MINIMIZE VARIATION IN POWER DENSITY

(75) Inventors: Jeremy D. Dando, Plymouth, MN (US); Timothy G. Curran, Ramsey, MN (US); Todd R. Stangenes, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 695 days.

(21) Appl. No.: 11/617,656

(22) Filed: Dec. 28, 2006

(65) Prior Publication Data

US 2008/0161788 A1 Jul. 3, 2008
US 2009/0076495 A2 Mar. 19, 2009

(51) Int. Cl.
*A61B 18/18* (2006.01)
(52) U.S. Cl. .............................. 606/41; 606/32; 606/34; 374/110; 374/166
(58) Field of Classification Search ............. 606/32–41; 374/110–114, 166
See application file for complete search history.

(56) References Cited

U.S. PATENT DOCUMENTS

| 5,023,945 | A | * | 6/1991 | Childs ........................ 398/161 |
| 5,115,818 | A | | 5/1992 | Holleman et al. |
| 5,334,193 | A | * | 8/1994 | Nardella ...................... 606/41 |
| 5,496,312 | A | * | 3/1996 | Klicek ......................... 606/34 |
| 5,540,681 | A | | 7/1996 | Strul et al. |
| 5,573,533 | A | | 11/1996 | Strul |
| 5,676,662 | A | | 10/1997 | Fleischhacker et al. |
| 5,755,790 | A | | 5/1998 | Chevillon et al. |
| 5,849,028 | A | | 12/1998 | Chen |
| 5,957,961 | A | | 9/1999 | Maguire et al. |
| 6,045,550 | A | | 4/2000 | Simpson et al. |
| 6,162,184 | A | | 12/2000 | Swanson et al. |
| 6,217,573 | B1 | | 4/2001 | Webster |
| 6,267,758 | B1 | | 7/2001 | Daw et al. |

(Continued)

OTHER PUBLICATIONS

National Semiconductor Application Note 31, in particular "Section 3—Signal Processing" on p. 17; Sep. 2002, 33 pages.
Demolin, et al., "Soft Thrombus Formation in Radiofrequency Catheter Ablation" PACE, vol. 25, No. 8, Aug. 2002, pp. 1219-1222.

(Continued)

*Primary Examiner*—Linda C Dvorak
*Assistant Examiner*—Amanda Scott
(74) *Attorney, Agent, or Firm*—Trenner Law Firm LLC

(57) ABSTRACT

A catheter is designed with a virtual electrode structure for creating a linear lesion. The catheter includes a sensor array that measures temperatures of adjacent tissue along the length of the virtual electrode section. The sensors in the sensor array include a conductive material that is substantially coated with an electrically and thermally insulating material. An aperture is formed in the insulating coating to expose an area of the conductive material. Leads are coupled with each sensor and are connected at their opposite, proximal ends with a discrimination circuit. The circuit processes the signals induced in the sensors to output a single temperature measurement, for example, the highest temperature, the lowest temperature, or the average temperature. The sensors also measure cardiac electrical activity and the leads are further connected to an electrocardiograph monitor to determine the efficacy of treatment.

20 Claims, 16 Drawing Sheets

U.S. PATENT DOCUMENTS

| | | |
|---|---|---|
| 6,322,584 B2 | 11/2001 | Ingle et al. |
| 6,346,104 B2 * | 2/2002 | Daly et al. .................... 606/34 |
| 6,356,790 B1 | 3/2002 | Maguire et al. |
| 6,605,087 B2 | 8/2003 | Swartz et al. |
| 6,984,232 B2 | 1/2006 | Vanney et al. |
| 7,357,800 B2 * | 4/2008 | Swanson .................... 606/39 |
| 2001/0020166 A1 | 9/2001 | Daly et al. |
| 2002/0128643 A1 | 9/2002 | Simpson et al. |

OTHER PUBLICATIONS

Bard Electrophysiology, "Orbiter PV—Variable Loop Mapping Catheter," Copyright 2004 C.R. Bard Inc., 6 pages.

International Search Report and Written Opinion of International Searching Authority for International Application PCT/US07/88587, Sep. 10, 2008, 13 pages.

* cited by examiner

ABLATION CATHETER WITH SENSOR ARRAY AND DISCRIMINATION CIRCUIT TO MINIMIZE VARIATION IN POWER DENSITY

BACKGROUND OF THE INVENTION a. Field of the Invention

The instant invention is directed toward a catheter with a virtual electrode section for ablation of tissue and a corresponding temperature sensor array. The temperature sensor array is part of a discrimination circuit that processes the temperature data for control of the energy source.

b. Background Art

A catheter is generally a very small diameter tube for insertion into the body for the performance of medical procedures. Among other uses, catheters can be used to examine, diagnose, and treat disease while positioned at a specific location within the body that is otherwise inaccessible without more invasive procedures. During these procedures a catheter is inserted into the patient's vasculature near the surface of the body and is guided to a specific location within the body for examination, diagnosis, and treatment. For example, one procedure utilizes a catheter to convey an electrical stimulus to a selected location within the human body. Another procedure utilizes a catheter with sensing electrodes to monitor various forms of electrical activity in the human body.

In a normal heart, contraction and relaxation of the heart muscle (myocardium) takes place in an organized fashion as electrochemical signals pass sequentially through the myocardium from the sinoatrial (SA) node located in the right atrium, to the atrialventricular (AV) node in the septum between the right atrium and right ventricle, and then along a well-defined route which includes the His-Purkinje system into the left and right ventricles. Sometimes abnormal rhythms occur in the atria which are referred to as atrial arrhythmia. Three of the most common arrhythmia are ectopic atrial tachycardia, atrial fibrillation, and atrial flutter. Arrhythmia can result in significant patient discomfort and even death because of a number of associated problems, including the following: (1) an irregular heart rate, which causes a patient discomfort and anxiety; (2) loss of synchronous atrioventricular contractions which compromises cardiac hemodynamics resulting in varying levels of congestive heart failure; and (3) stasis of blood flow, which increases the vulnerability to thromboembolism.

It is sometimes difficult to isolate a specific pathological cause for the arrhythmia although it is believed that the principal mechanism is one or a multitude of stray circuits within the left and/or right atrium. These circuits or stray electrical signals are believed to interfere with the normal electrochemical signals passing from the SA node to the AV node and into the ventricles. Efforts to alleviate these problems in the past have included significant usage of various drugs. In some circumstances drug therapy is ineffective and frequently is plagued with side effects such as dizziness, nausea, vision problems, and other difficulties.

An increasingly common medical procedure for the treatment of certain types of cardiac arrhythmia and atrial arrhythmia involves the ablation of tissue in the heart to cut off the path for stray or improper electrical signals. The particular area for ablation depends on the type of underlying arrhythmia. Originally, such procedures actually involved making incisions in the myocardium (hence the term ablate, which means to cut) to create scar tissue that blocked the electrical signals. These procedures are now often performed with an ablation catheter.

Ablation catheters do not physically cut the tissue. Instead they are designed to apply electrical energy to areas of the myocardial tissue and cause tissue necrosis by coagulating the blood supply in the tissue and thus halting new blood flow to the tissue area. The necrosis lesion produced electrically isolates or renders the tissue non-contractile. The lesion partially or completely blocks the stray electrical signals to lessen or eliminate arrhythmia. Typically, the ablation catheter is inserted in an artery or vein in the leg, neck, or arm of the patient and threaded, sometimes with the aid of a guide wire or introducer, through the vessels until a distal tip of the ablation catheter reaches the desired location for the ablation procedure in the heart.

It is well known that benefits may be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, when sufficiently deep lesions are formed at specific locations in cardiac tissue via coagulation necrosis, undesirable ventricular tachycardias and atrial flutter may be lessened or eliminated. "Sufficiently deep" lesions means transmural lesions in some cardiac applications.

It has been discovered that more effective results may be achieved if a linear lesion of cardiac tissue is formed. The term "linear lesion" as used herein means an elongate, continuous lesion, whether straight or curved, that blocks electrical conduction. The ablation catheters commonly used to perform these procedures produce electrically inactive or noncontractile tissue at a selected location by physical contact of the cardiac tissue with an electrode of the ablation catheter. Current techniques for creating continuous linear lesions in endocardial applications include, for example, dragging a conventional catheter on the tissue, using an array electrode, or using pre-formed curved electrodes. Curved electrodes have also been formed by guiding a catheter with an array electrode over a wire rail. The wire rail is formed as a loop, thus guiding the distal end of the catheter into a loop form as well. The array electrodes and curved electrodes are generally placed along the length of tissue to be treated and energized to create a lesion in the tissue contiguous with the span of electrodes along the curved or looped surface. Alternately, some catheter designs incorporate steering mechanisms to direct an electrode at the distal tip of the catheter. The clinician places the distal tip electrode of the catheter on a targeted area of tissue by sensitive steering mechanisms and then relocates the electrode tip to an adjacent tissue location in order to form a continuous lesion.

The effectiveness of these procedures depends on a number of variables including the position and contact pressure of the tip electrode of the ablation catheter against the cardiac tissue, the time that the tip electrode of the ablation catheter is placed against the tissue, the amount of coagulum that is generated as a result of heat generated during the ablation procedure, and other variables associated with a beating heart, especially an erratically beating heart. One difficulty in obtaining an adequate ablation lesion using conventional ablation catheters is the constant movement of the heart, especially when there is an erratic or irregular heart beat. Another difficulty in obtaining an adequate ablation lesion is caused by the inability of conventional catheters to obtain and retain uniform contact with the cardiac tissue across the entire length of the ablation electrode surface.

Without such continuous and uniform contact, any ablation lesions formed may not be adequate. Unless an uninterrupted track of cardiac tissue is ablated, non-ablated tissue or incompletely ablated tissue may remain electrically active, permitting the continuation of the stray circuit that causes the arrhythmia. Conventional tip electrodes with adjacent ring electrodes are not preferred for this type of procedure, however, because of the high amount of energy that is necessary to ablate sufficient tissue to produce a complete linear lesion. Also, conventional ring electrode ablation may leave holes or gaps in a lesion, which can provide a pathway along which unwanted electrochemical signals can travel.

During conventional ablation procedures, the ablating energy is delivered directly to the cardiac tissue by an electrode on the catheter placed against the surface of the tissue to raise the temperature of the tissue to be ablated. This rise in tissue temperature also causes a rise in the temperature of blood surrounding the electrode. This often results in the formation of coagulum on the electrode, which reduces the efficiency of the ablation electrode. With direct contact between the electrode and the blood, some of the energy targeted for the tissue ablation is dissipated into the blood. To achieve efficient and effective ablation, coagulation of blood that is common with conventional ablation catheters should be avoided. This coagulation problem can be especially significant when linear ablation lesions or tracks are produced because such linear ablation procedures conventionally take more time than ablation procedures ablating only a single location.

Another particular difficulty encountered with existing ablation catheters is assurance of adequate tissue contact. Many catheters use rigid electrodes that do not always conform to the tissue surface, especially when sharp gradients and undulations are present, such as at the ostium of the pulmonary veins in the left atrium and the isthmus of the right atrium between the inferior vena cava and the tricuspid valve. Consequently, continuous linear lesions are difficult to achieve. With present rigid catheters of uniform construction, it can be quite difficult to maintain sufficient contact pressure until an adequate lesion has been formed. This problem is exacerbated on contoured or trabecular surfaces. If the contact between the electrode and the tissue cannot be properly maintained, a quality lesion is unlikely to be formed.

To address the coagulation concern, more recent designs of ablation electrodes transfer energy to the target tissue with a conductive fluid medium that passes over a standard metal electrode rather than contacting the standard electrode to the tissue. The fluid flow thus reduces the likelihood that coagulum will form on any of the surfaces of the electrode. These so-called "virtual electrodes" also help reduce tissue charring because the fluid, while energized, also acts as a cooling heat transfer medium.

Even though virtual electrodes have certain benefits over standard electrodes, an ablation procedure still requires that the temperature of the target tissue be raised to a certain level to achieve necrosis and form an adequate lesion. However, when creating a relatively long, linear lesion during a single application of energy, it can be difficult to control the energy output over the entire length of the electrode-tissue interface. Some points along the interface may be hotter than others. Care must be taken to prevent the excessive application of energy, which can result in tissue damage beyond mere necrosis and instead actually decompose, i.e., char, the tissue. Such excessive tissue damage can ultimately weaken and compromise the myocardium.

The information included in this background section of the specification, including any references cited herein and any description or discussion thereof, is included for technical reference purposes only and is not to be regarded subject matter by which the scope of the invention is to be bound.

BRIEF SUMMARY OF THE INVENTION

The present invention is directed to a cardiac catheter ablation system with several novel features that offer improvements both individually and in combination. These features include a catheter design, a sensor design, a circuit design, and the system design itself. The catheter is designed with a virtual ablation electrode structure for creating a linear lesion. It further includes a sensor array that measures temperatures of adjacent tissue along the length of the virtual electrode section. The sensors in the sensor array include a conductive material that is substantially coated with an electrically and thermally insulating material. An aperture is formed in the insulating coating to expose an area of the conductive material. The leads coupled with each sensor are connected at their opposite, proximal ends with a discriminator circuit. The circuit processes the signals induced in the sensors to output a single temperature measurement, for example, one or more of the single highest temperature, the single lowest temperature, or another temperature measurement calculated from one or more signal received from the sensors of the sensor array. The sensors can also measure cardiac electrical activity and the leads are further connected to an electrocardiograph monitor to determine the efficacy of treatment.

By using common sensors for thermal and cardiac electrical sensing it is possible to reduce the number of electrical leads and connections required for temperature sensing and electrical sensing and thus reduce the cross-sectional area of the catheter. Further, by simultaneously sensing temperature and electrical signals, constant temperature and electrical feedback is available to gauge the progress of the ablation procedure and the corresponding thermal necrosis of the tissue.

One embodiment of the invention is a catheter having an elongate shaft that defines a fluid lumen. The elongate shaft is primarily composed of a proximal section and a virtual electrode ablation section at a distal end that is in fluid communication with the fluid lumen. A plurality of sensors is positioned along the virtual electrode ablation section of the elongate shaft. Each of the plurality of sensors can be composed of a conductive material and an insulating coating substantially covering the conductive material. The insulating coating can define a sensing aperture that exposes an area of the conductive material. A plurality of sensor leads extend from the virtual electrode ablation section to the proximal section. Each of the plurality of sensor leads is coupled with a respective one of the plurality of sensors.

Another embodiment of the invention is a circuit for discriminating between a plurality of temperature measurements received from an array of sensors positioned on an ablation catheter. The circuit has an input signal receiving component for receiving a plurality of input signals. Each of the plurality of input signals corresponds to a respective one of the plurality of temperature measurements. The circuit also has a plurality of amplifier components. Each amplifier component has a first input, a second input, and an output. The first input of each amplifier component is coupled with the input signal receiving component and receives a respective one of the plurality of input signals. The circuit further includes a plurality of rectifier components. Each rectifier component has a first terminal and a second terminal. The first terminal of each rectifier component is coupled with the output of a respective one of the plurality of amplifier components. In addition, the circuit includes a feedback loop coupled with the second terminal of each of the plurality of rectifier components and further coupled with the second input of each of the plurality of amplifier components. The voltage level of the feedback loop substantially follows a voltage received at one of the plurality of the input signal receiving components. The circuit also has an output component coupled with the feedback loop to provide a single output signal corresponding to the voltage level of the feedback loop for use by an energy source.

An additional embodiment of the invention is a system for discriminating between a plurality of temperature measurements during the performance of a cardiac ablation procedure. The system includes a catheter, a circuit, and an energy source. The catheter is composed of an elongate shaft that defines a fluid lumen. The elongate shaft has a proximal section and a virtual electrode ablation section at a distal end that is in fluid communication with the fluid lumen. An electrode lead extends through the proximal section to distal end and is electrically exposed within the fluid lumen in the virtual electrode ablation section. A plurality of sensors is positioned along the virtual electrode ablation section of the elongate shaft. Each of the plurality of sensors includes a conductive material and an insulating coating substantially covering the conductive material. The insulating coating defines a sensing aperture that exposes an area of the conductive material. A plurality of sensor leads extend from the virtual electrode ablation section to the proximal section. Each of the plurality of sensor leads is coupled with a respective one of the plurality of sensors.

The circuit is composed of an input signal receiving component, which receives a plurality of input signals from the plurality of sensor leads. Each of the plurality of input signals corresponds to a respective temperature measurement received from a respective one of the plurality of sensors. The circuit also has a plurality of amplifier components. Each amplifier component has a first input, a second input, and an output. The first input of each amplifier component is coupled with the signal receiving component for receiving a respective one of the plurality of input signals from a respective one of the plurality of sensors. The circuit further includes a plurality of rectifier components. Each rectifier component has a first terminal and a second terminal. The first terminal of each rectifier component is coupled with the output of a respective one of the plurality of amplifier components. The circuit also includes a feedback loop coupled with the output of each of the plurality of rectifier components and further coupled with the second input of each of the plurality of amplifier components. The voltage level on the feedback loop substantially follows a voltage received at one of the plurality of the input signal receiving components. The circuit additionally has an output component coupled with the feedback loop to provide a single output signal corresponding to the voltage level on the feedback loop.

The energy source additionally has an input electrically coupled with the output component of the circuit and an output electrically coupled with the electrode lead.

A further embodiment of the invention is a sensor for use in conjunction with a cardiac ablation catheter. The sensor is composed of a conductive band that encircles an outer surface of the catheter. An insulating coating substantially covers an outer surface of the conductive band. The insulating coating defines a sensing aperture exposing a portion of the conductive band. The sensor also has at least one lead wire electrically coupled with the conductive band.

Other features, details, utilities, and advantages of the present invention will be apparent from the following more particular written description of various embodiments of the invention as further illustrated in the accompanying drawings and defined in the appended claims.

DETAILED DESCRIPTION OF THE INVENTION

The present invention concerns an improved design for catheters, such as ablation catheters used, for example, in cardiac ablation procedures to produce linear lesions in cardiac tissue. In one embodiment, the electrode structure on the distal end of the catheter of the present invention is generally termed a "virtual electrode." In a virtual electrode design, ablation energy is primarily imparted to the target tissue via energy transfer through a conductive fluid medium escaping the distal end of the catheter rather than by actual contact of a traditional electrode with the tissue. In another embodiment, the present invention is directed to a temperature sensing system for use in a catheter, such as an ablation catheter, whether the catheter is a traditional electrode catheter or a virtual electrode. The temperature sensing system, for example, may be used with the virtual electrode of a cardiac ablation catheter. The temperature sensing system includes physical sensors on the catheter and a temperature discrimination circuit for passing temperature information, such as to an RF generator of a cardiac ablation catheter system.

Figure 1:
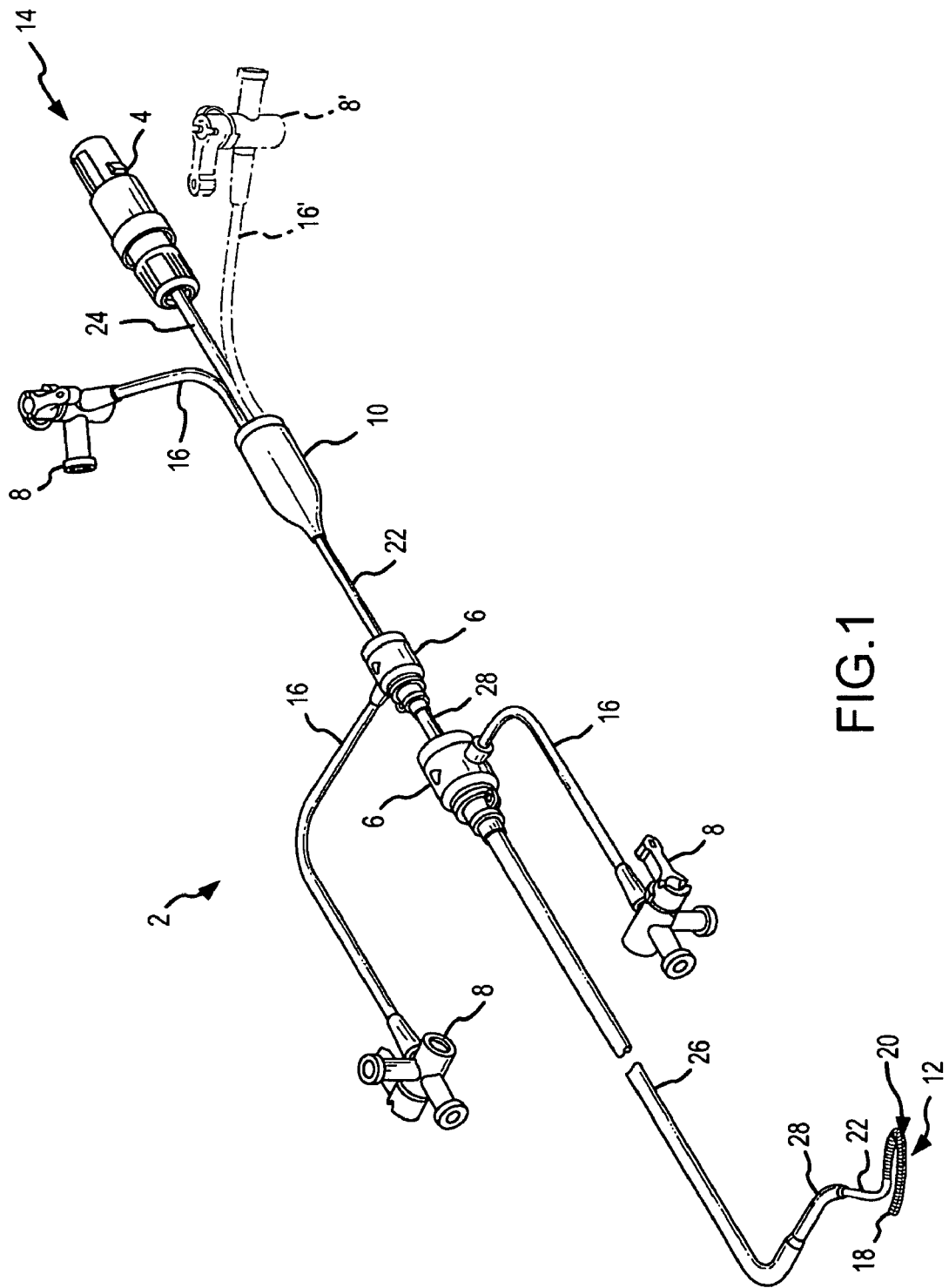
FIG. 1 is an isometric view of an ablation catheter/introducer assembly including a virtual electrode section with a sensing array according to a generic embodiment of the present invention.

FIG. 1 is an isometric view of a catheter/introducer assembly 2 for use in conjunction with the present invention. A catheter 22 is formed as an elongate shaft with an electrical connector 4 at a proximal end 14 and an ablation electrode section 20 at a distal end 12. The ablation electrode section 20, according to a generic embodiment of the present invention, is used in combination with an inner guiding introducer 28 and an outer guiding introducer 26 to facilitate formation of lesions on tissue, for example, cardiovascular tissue. The inner guiding introducer 28 is longer than and is inserted within a lumen of the outer guiding introducer 26. Alternatively, a single guiding introducer or a precurved transeptal sheath may be used instead of both the inner guiding introducer 28 and the outer guiding introducer 26. In general, introducers or precurved sheaths are shaped to facilitate placement of the ablation electrode section 20 at the tissue surface to be ablated. As depicted in FIG. 1, for example, the outer guiding introducer 26 may be formed with a curve at the distal end 12. Similarly, the inner guiding introducer 28 may be formed with a curve at the distal end 12. Together, the curves in the guiding introducers 26, 28 help orient the catheter 22 as it emerges from the inner guiding introducer 26 in a cardiac cavity. Thus, the inner guiding introducer 28 and the outer guiding introducer 26 are used, for example, to navigate a patient's vasculature to the heart and through its complex physiology to reach specific tissue to be ablated. The guiding introducers 26, 28 need not be curved or curved in the manner depicted depending upon the desired application.

As shown in FIG. 1, each of the guiding introducers 26, 28 is connected with a hemostatic valve 6 at its proximal end to prevent blood or other fluid that fills the guiding introducers 26, 28 from leaking before the insertion of the catheter 22. The hemostatic valves 6 form tight seals around the shafts of the guiding introducers 26, 28 or the catheter 22 when inserted therein. Each hemostatic valve 6 may have a port connected with a length of tubing 16 to a fluid introduction valve 8. The fluid introduction valves 8 may be connected with a fluid source, for example, saline or a drug, to easily introduce the fluid into the introducers, for example, to flush the introducer or to inject a drug in to the patient. Each of the fluid introduction valves 8 may control the flow of fluid into the hemostatic valves 6 and thereby the guiding introducers 26, 28.

The proximal end 14 of the catheter 22 may include a catheter boot 10 that seals around several components to allow the introduction of fluids and control mechanisms into the catheter 22. For example, at least, one fluid introduction valve 8 with an attached length of tubing 16 may be coupled with the catheter boot 10. An optional fluid introduction valve 8' and correlative tube 16' (shown in phantom) may also be coupled with the catheter boot 10, for example, for the introduction of fluid into a catheter with multiple fluid lumens if separate control of the pressure and flow of fluid in the separate lumens is desired. The electrical connector 4 for connection with a control handle, an energy generator, and/or sensing equipment (none shown) may be coupled with the catheter boot 10 via a control shaft 24. The control shaft 24 may enclose, for example, control wires for manipulating the catheter 22 or ablation electrode section 20, conductors for energizing an electrode in the ablation electrode section 20, and/or lead wires for connecting with sensors in the ablation electrode section 20. The catheter boot 10 provides a sealed interface to shield the connections between such wires and fluid sources and one or more lumens in the catheter 22 through which they extend.

The catheter 22 may be constructed from a number of different polymers, for example, polypropylene, oriented polypropylene, polyethylene, polyethylene terephthalate, crystallized polyethylene terephthalate, polyester, polyvinyl chloride (PVC), polytetraflouroethylene (PTFE), expanded polytetraflouroethylene (ePTFE), and Pellethane®. Alternatively, the catheter 22 may be composed, for example, of any of several formulations of Pebax® resins (AUTOFINA Chemicals, Inc., Philadelphia, Pa.), or other polyether-block co-polyamide polymers. By using different formulations of the Pebax® resins for different sections of the catheter 22, different material and mechanical properties, for example, flexibility or stiffness, can be chosen for different sections along the length of the catheter 22.

The catheter 22 may also be a braided catheter wherein the catheter wall includes a cylindrical and/or flat braid of metal fibers (not shown), for example, stainless steel fibers. Such a metallic braid may be included in the catheter 22 to add stability to the catheter 22 and also to resist radial forces that might crush the catheter 22. Metallic braid also provides a framework to translate torsional forces imparted by the clinician on the proximal end 14 of the catheter 22 to the distal end 12 to rotate the catheter 22 for appropriate orientation of the ablation electrode section 20.

The distal end of the catheter may be straight or take on a myriad of shapes depending upon the desired application. The distal end 12 of one embodiment of a catheter 22 according to the present invention is shown in greater detail in FIGS. 2 and 3. In the embodiment shown in FIGS. 2 and 3, the catheter 22 consists mainly of a "straight" section 30 extending from the catheter boot 10 at the proximal end 14 to a point, adjacent to the distal end 12 of the catheter/introducer assembly 2 (see the exemplary catheter of FIG. 1.). The straight section 30 is generally the portion of the catheter 22 that remains within the vasculature of the patient while a sensing or ablation procedure is performed by a clinician. At the distal end 12 the catheter 22 is composed of a first curved section 32 and a second curved section 34 before transitioning into a third curved section 36 that forms the ablation electrode. The first curved section 32 is adjacent and distal to the straight section 30 and proximal and adjacent to the second curved section 34. The second curved section 34 is itself proximal and adjacent to the third curved section 36.

The straight section 30, first curved section 32, second curved section 34, and third curved section 36 may together form a single, unitary structure of the catheter 22, but may originally be separate pieces joined together to form the catheter 22. For example, as indicated above, each of the different sections of the catheter may be composed of different formulations of Pebax® resins, or other poly ether-block co-polyamide polymers, which can be used to create desired material stiffness within the different sections of the catheter. By joining separate curved sections or unitarily molding the distal end of the catheter shaft 22 proximal to the ablation electrode section 20 using a relatively stiff resin, a desired shape can be imparted to that section of the catheter 22 to effect the ultimate orientation of the ablation electrode section 20.

Figure 2:
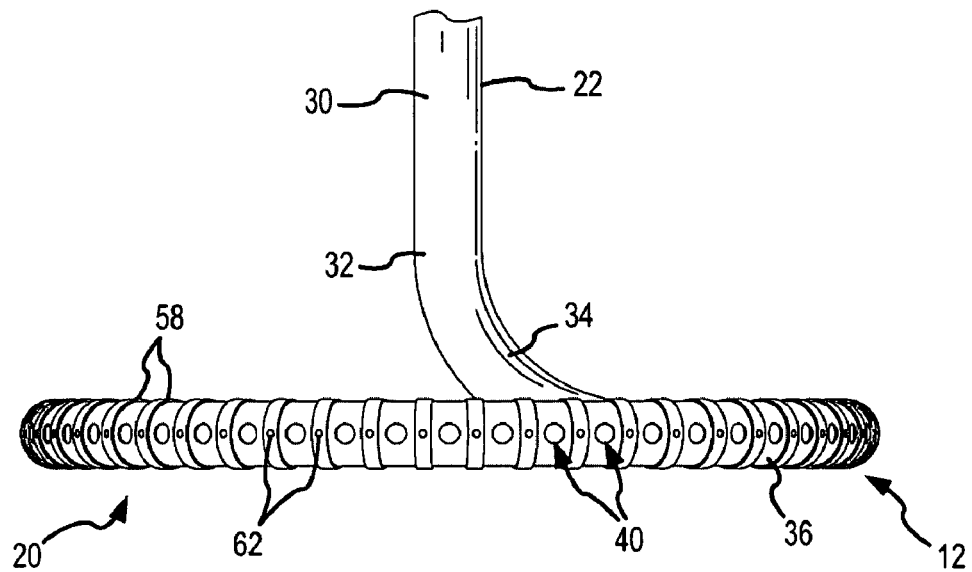
FIG. 2 is an elevation view of a distal portion of a catheter, including a virtual electrode section, according to one embodiment of the present invention.
Figure 3:
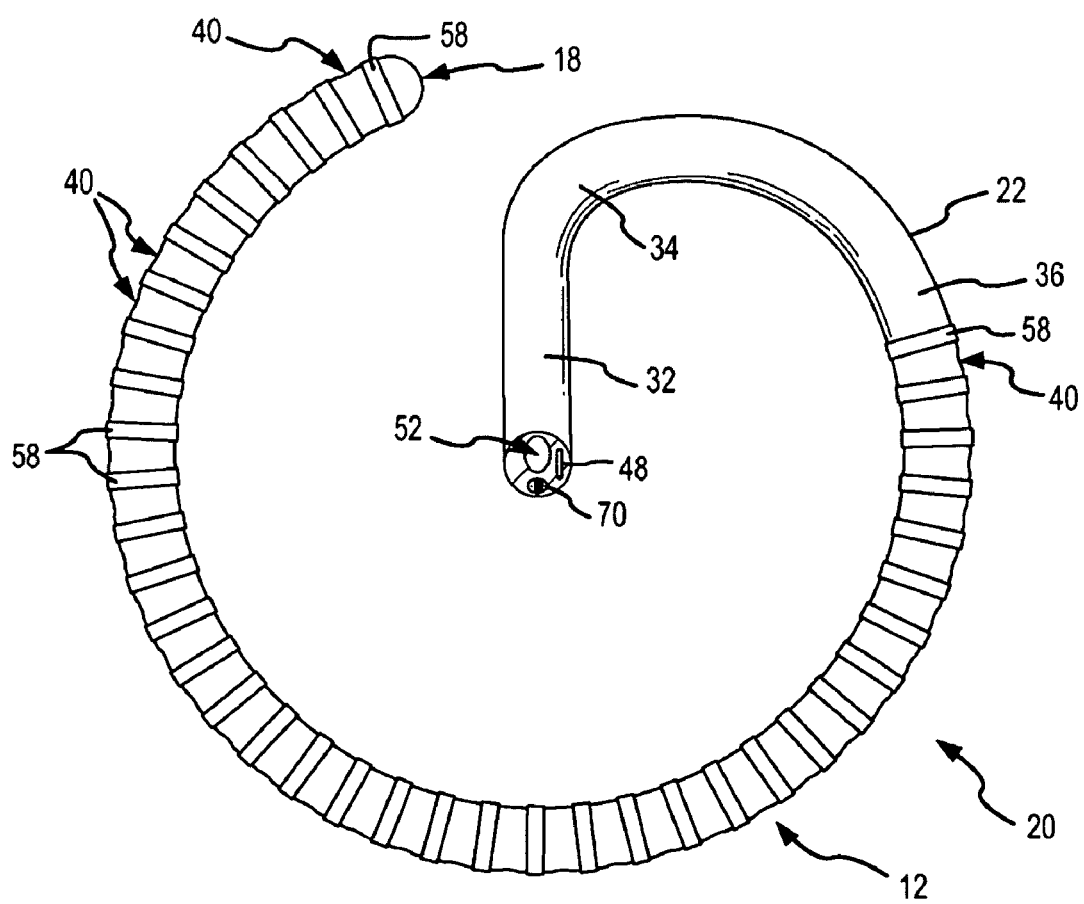
FIG. 3 is a top plan view of the catheter of FIG. 2.
Figure 4:
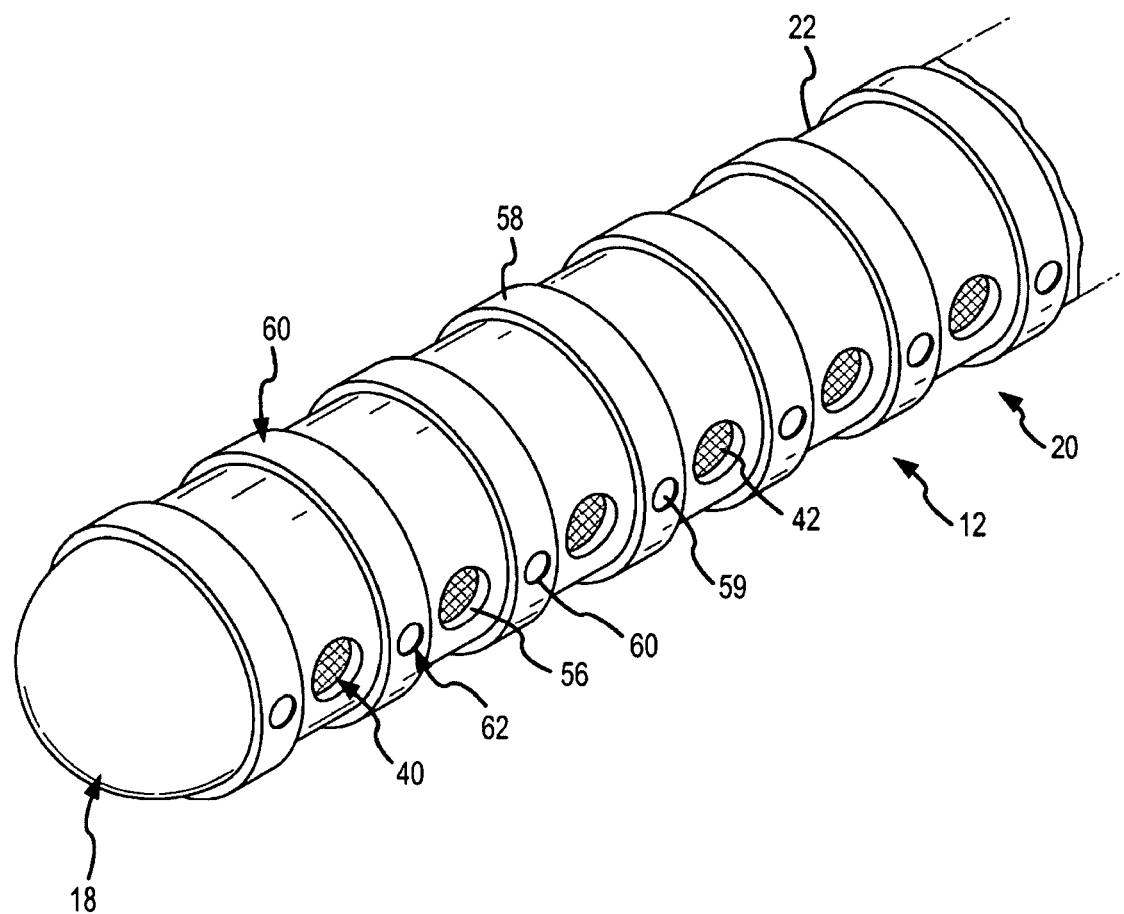
FIG. 4 is an isometric view of the distal end of the catheter of FIG. 2.

As shown in FIGS. 2 and 3, the first curved section 32 and second curved section 34 of the catheter 22 align the third curved section 36 such that it is transverse to the orientation of the straight section 30 of the catheter 22. The ablation electrode section 20 assumes the shape of the third curved section 36 and forms a generally C-shaped or lasso-like configuration when deployed from the inner guiding introducer 28. In addition, the distal end of the straight section 30 of the catheter 22 is oriented in a position where a longitudinal axis extending through the distal end of the straight section 30 passes orthogonally through the center of a circle defined by the C-shaped third curved section 36. In this manner the straight section 30 of the catheter 22 is spatially displaced from the ablation electrode section 20 so that the straight section 30 is unlikely to interfere with the interface between the ablation electrode section 20 extending along the third curved section 36 and the cardiac tissue as further described below.

Figure 5:
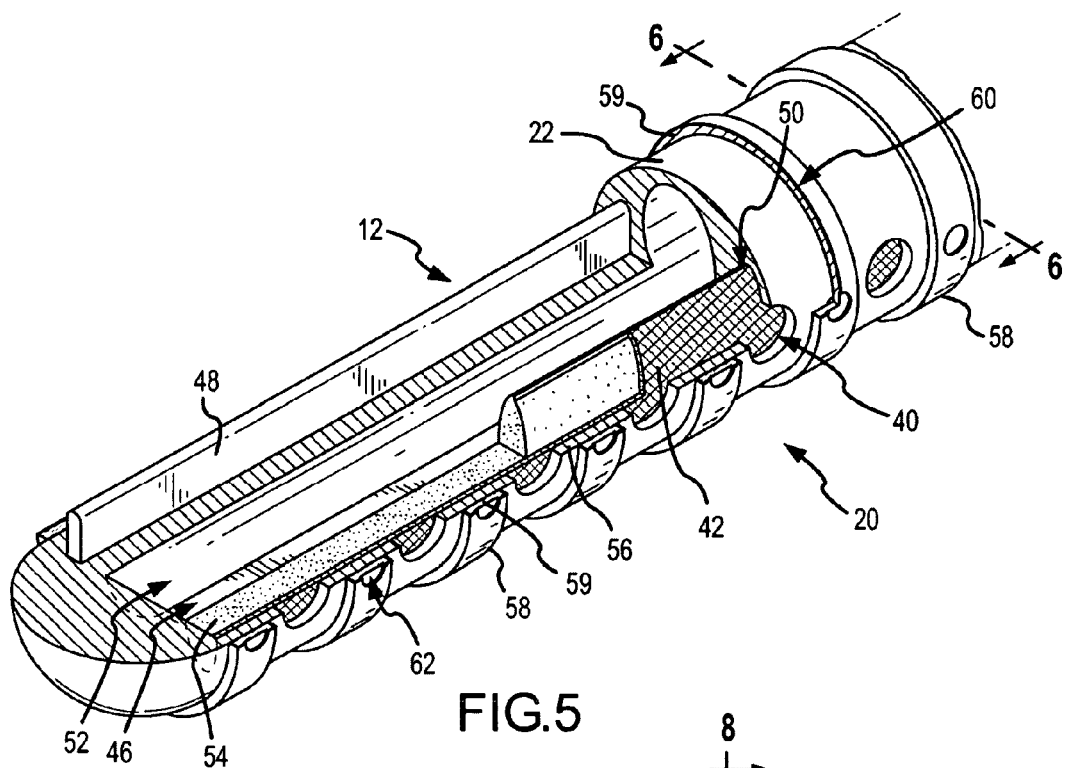
FIG. 5 is an isometric view with a partial cut-away of the catheter of FIG. 2.

The catheter 22 may further house a shape-retention or shape-memory wire 48 in order to impart a desired shape to the distal end 12 of the catheter 22 in the area of the ablation electrode section 20. See also FIGS. 5-7. A shape-retention or shape-memory wire 48 is flexible while a clinician negotiates the catheter 22 through the vasculature to reach the heart and enter an atrial chamber. Once the distal end 12 of the catheter 22 reaches the desired cardiac cavity with the ablation electrode section 20, the shape-retention/shape-memory wire 48 can be caused to assume a pre-formed shape form, e.g., the C-shaped configuration of the ablation electrode section 20, to accurately orient the ablation electrode section 20 within the cardiac cavity for the procedure to be performed. The C-shaped configuration of the ablation electrode section 20 as shown in FIGS. 2 and 3 may be imparted to the catheter through the use of such shape-retention or shape-memory wires, in addition to or in lieu of pre-molding of the catheter material, to appropriately conform to tissue or to the shape of a cavity in order to create the desired lesion at a desired location.

In one embodiment, the shape-retention/shape-memory wire 48 may be NiTinol wire, a nickel-titanium (NiTi) alloy, chosen for its exceptional shape-retention/shape-memory properties. When used for shape-memory applications, metals such as NiTinol are materials that have been plastically deformed to a desired shape before use. Then upon heat application, either from the body as the catheter is inserted into the vasculature or from external sources, the shape-memory material is caused to assume its original shape before being plastically deformed. A shape-memory wire generally exhibits increased tensile strength once the transformation to the pre-formed shape is completed. NiTinol and other shape-memory alloys are able to undergo a "martenistic" phase transformation that enables them to change from a "temporary" shape to a "parent" shape at temperatures above a transition temperature. Below the transition temperature, the alloy can be bent into various shapes. Holding a sample in position in a particular parent shape while heating it to a high temperature programs the alloy to remember the parent shape. Upon cooling, the alloy adopts any temporary shape imparted to it, but when heated again above the transition temperature, the alloy automatically reverts to its parent shape Common formulas of NiTinol have transformation temperatures ranging between −100 and +110° C., have great shape-memory strain, are thermally stable, and have excellent corrosion resistance, which make NiTinol exemplary for use in medical devices for insertion into a patient. For example, the shape-memory wire may be designed using NiTinol with a transition temperature around or below room temperature.

Before use the catheter is stored in a low-temperature state. By flushing the fluid lumen with chilled saline solution, the NiTinol shape-memory wire can be kept in the deformed state while positioning the catheter at the desired site. When appropriately positioned, the flow of chilled saline solution can be stopped and the catheter, either warmed by body heat or by the introduction of warm saline, promotes recovery by the shape-memory wire to assume its "preprogrammed" shape, forming, for example, the C-shaped curve of the ablation electrode section.

Alternately, or in addition, shape-memory materials such as NiTinol may also be super elastic—able to sustain a large deformation at a constant temperature—and when the deforming force is released they return to their original, undeformed shape. Thus a catheter 22 incorporating NiTinol shape-retention wire 48 may be inserted into the generally straight lengths of introducer sheaths to reach a desired location and upon emerging from the introducer, the shape-retention wire 48 will assume its "preformed" shape. The shape-retention wire 48 is flexible while a clinician negotiates the catheter 22 through the vasculature to reach the heart and enter an atrial chamber. Once the distal end 12 of the catheter 22 reaches the desired cardiac cavity with the ablation electrode section 20, the shape-retention wire 48 assumes a pre-formed shape form, e.g., the C-shaped configuration of the ablation electrode section 20, to accurately orient the ablation electrode section 20 within the cardiac cavity for the procedure to be performed.

As further shown in FIGS. 2 and 3, the distal end 12 of the ablation electrode section 20 of the catheter 22 is composed in part of a linear array of ports 40 formed at an exterior wall of the catheter 22. In an exemplary embodiment, the ports 40 are circular and arranged along the outside curve of the third curved section 36 of the catheter 22. It should be noted that in other embodiments the ports 40 could be other geometries and/or positioned in another location on the outside surface of the catheter wall, for example, the bottom wall of the catheter 22 with reference to the orientation of the catheter 22 as depicted in FIG. 2. The ports 40 emit energized conductive fluid from within the catheter 22 whereby the ablation electrode section 20 operates as a virtual electrode as further described herein.

An array of sensor rings 58 is also provided along the ablation electrode section 20 of the catheter 22. As shown in FIGS. 2 and 3, a respective sensor ring 58 is positioned between each pair of adjacent ports 40. An additional sensor ring 58 is positioned adjacent and distal to the most distal port 40 at the distal tip 18 of the catheter 22. Similarly, a sensor ring 58 is positioned proximal and adjacent to the most proximal port 40. In this manner, each of the ports 40 is bounded on either side by a sensor ring 58. It should be noted that in some embodiments, fewer sensor rings may be used, for example, wherein two or more ports are bounded by a pair of sensor rings. Each of the sensor rings 58 defines a sensor opening 62, the structure and function of which are further described below. Additionally, as shown in FIG. 3, the catheter 22 may house a fluid lumen 52, a wire lumen 70, and a shape retention wire 48.

FIGS. 4-8 depict a portion of the ablation electrode section 20 at the distal end 12 of the catheter 22 in greater detail. The catheter 22 as depicted in FIGS. 4-8 is presented in a straight, linear form as opposed to the curved form of FIGS. 2 and 3 for ease of depiction of the structures therein. As previously noted, the distal end 12 of the catheter 22 may be caused to take on any of a number of desired shapes depending upon the intended application of the catheter 22 as further described herein below.

Figure 6:
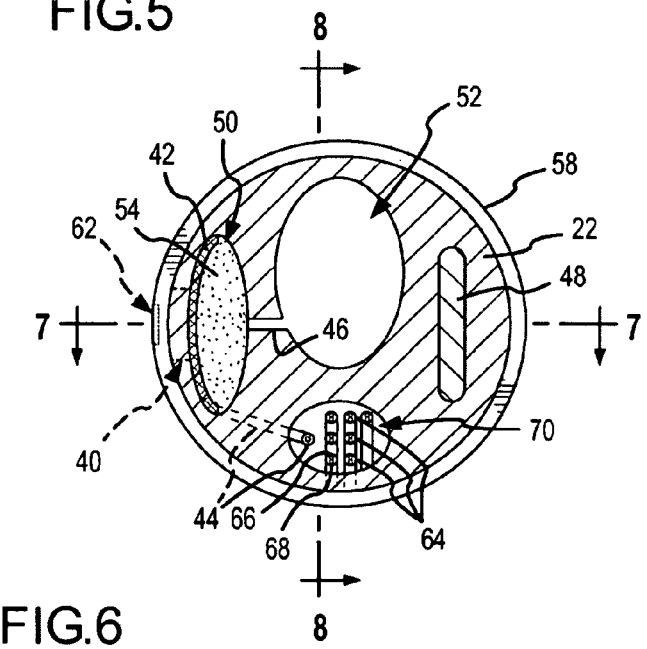
FIG. 6 is a cross-section view of the catheter of FIG. 2 taken along line 6-6 as indicated in FIG. 5.
Figure 7:
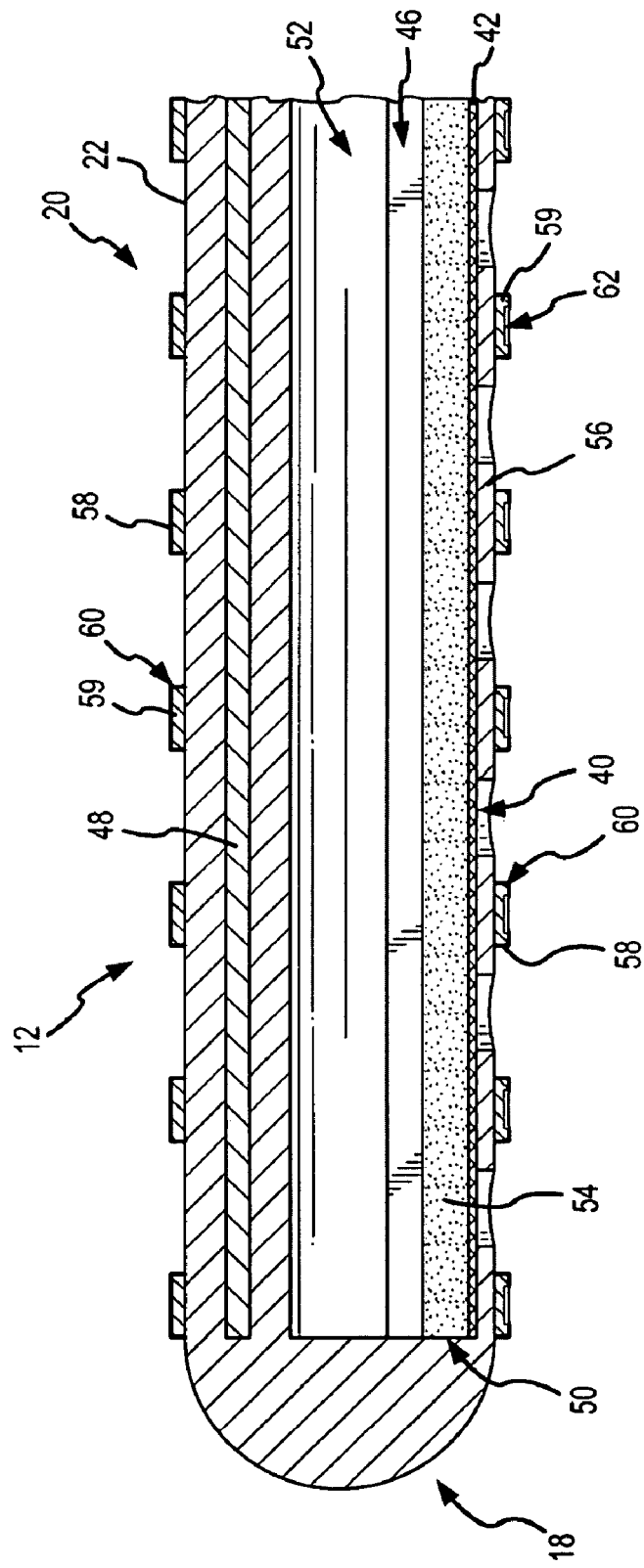
FIG. 7 is a cross-section view of the catheter of FIG. 2 taken along line 7-7 as indicated in FIG. 6.
Figure 8:
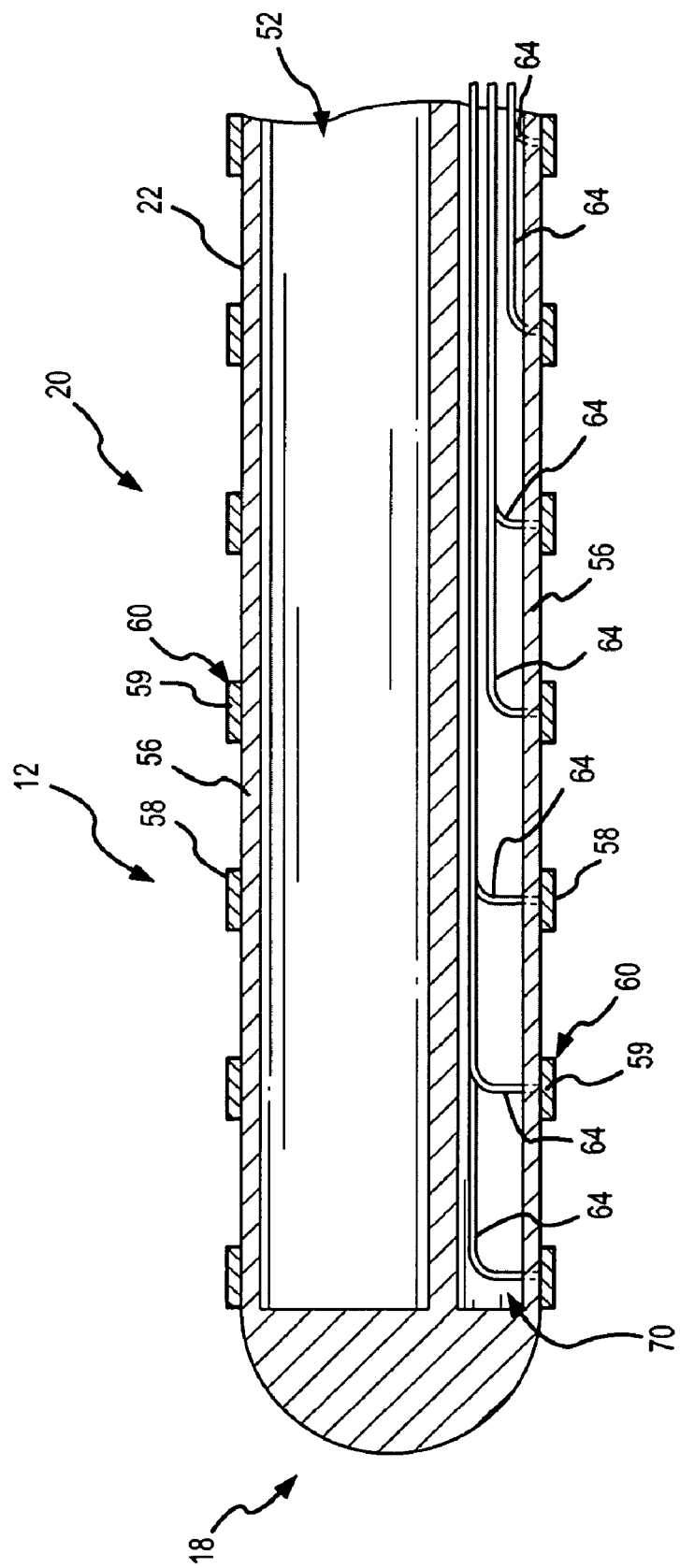
FIG. 8 is a cross-section view of the catheter of FIG. 2 taken along line 8-8 as indicated in FIG. 6.

As indicated above, the catheter 22 defines a central fluid lumen 52 and a wire lumen 70, and further houses a shape-retention wire 48 as shown to good advantage in FIG. 6. In addition, the catheter 22 defines an irrigation cavity 50 at its distal end that is in fluid communication with the fluid lumen 52 via a dispersion opening 46. The irrigation cavity 50 bounded on one side by the exterior wall 56 of the catheter 22 and thus is similarly in fluid communication with the ports 40 formed in the exterior wall 56 of the catheter 22. The dispersion opening 46 may be a linear slot (as shown) or a series of apertures within the catheter body that allows fluid to flow from the fluid lumen 52 to the irrigation cavity 50. The irrigation cavity 50 is primarily filled with a porous material 54. One side of the irrigation cavity 50 may also be lined with a mesh material 42 adjacent the exterior wall 56 of the catheter 22. The mesh material 42 is interposed between the porous material 54 and the ports 40 and functions as an electrode. It should be noted that this is merely one embodiment of a virtual electrode and many other embodiments may be used in conjunction with the present invention. For example, a simple virtual electrode structure including series of apertures defined in the catheter wall and extending into a fluid lumen housing a wire electrode lead could likewise be used.

In the embodiment of FIGS. 4-8, the porous material 54 may be composed of any of a number of micro-porous or macro-porous materials for example, polyvinyl alcohol (PVA), polytetrafluroethylene (PTFE), expanded polytetrafluroethylene (ePTFE), porous polyethylene, and porous polypropylene. In some applications, the porous material may also be composed of collagen. The mesh material 42 may be a wire mesh of platinum, platinum-iridium, platinum-tungsten, gold, stainless steel, or other biocompatible conductive metal. In other embodiments (not depicted herein), the mesh material may be a metal coating on a surface of the porous material, whereby the coated surface of the porous material may also act as the electrode.

The porous material 54 is provided as a buffer to reduce any impact of the pressure drop along the fluid lumen 52. In some applications, it is desirable to create such greater uniformity in fluid flow. In some instances, because of the pressure drop along the fluid lumen 52, a non-uniform flow of conductive fluid out of the ports 40 in the ablation electrode section 20 of the catheter 22 causes part of a linear lesion to be under-ablated because of excessive cooling by the fluid while part, of the linear lesion is over-ablated and charred because of too little fluid cooling. When porous material 54 is added between the fluid lumen 52 and the exit ports 40 in the ablation electrode section 20 of the catheter 22, the pressure drop as the conductive fluid crosses the porous material 54 is much higher than the pressure drop of the fluid in the fluid lumen 52. Further, the flow rate of conductive fluid exiting the catheter 22 is significantly reduced. By reducing the significance of the pressure drop of the fluid in the fluid lumen 52 and reducing the flow rate, a uniform distribution of fluid flow emerging from ports 40 the ablation electrode section 20 can be achieved.

The ports 40 may have a measurable depth within the exterior catheter wall 56 between the outer surface of the catheter 22 and a surface of the mesh electrode 42. As a result, there is a set-off distance between the mesh electrode 42 and the tissue surface to be ablated. In addition, the depth of the sensor rings 58 on the surface of the catheter 22 help to increase the set-off distance. This set-off distance avoids direct contact between the mesh electrode 42 and the tissue. Thus, the increase in the uniformity of fluid distribution by interposing the irrigation cavity 50 filled with porous material 54 between the fluid lumen 52 and the ports 40, and the creation of a set-back for the mesh material 42 from the tissue to be ablated, together greatly reduce the potential for charring of tissue.

The wire lumen 70 houses an array of sensor leads 64, which travel from the electrical connector 4 at the proximal end 14 of the catheter assembly 2 to the distal end 12 of the catheter 22. Each of the sensor leads 64 is composed of a copper wire 66 and a constantan wire 68, which together form the thermocouple at a particular sensor ring 58 as further described below. The wire lumen 70 further houses an electrode lead wire 44, which is coupled with the metal mesh material 42 in order to transmit RF energy to the mesh material 42 and energize it as an electrode.

Each of the sensor rings 58 is formed of a conductive band 59 attached circumferentially about the outer surface of the catheter 22 and is positioned between adjacent ports 40. The conductive band 59 may be composed of platinum, platinum-iridium, platinum-tungsten, gold, stainless steel, or other biocompatible conductive material. The conductive bands 59 of each sensor ring 58 have a thermally and electrically insulating surface coating 60. The surface coating 60 may be a thermoplastic or thermoset polymer material. Exemplary thermoplastic materials are polyester and polyamide. An exemplary thermoset material would be polyimide. An aperture is formed in the surface coating 60 to create a sensor opening 62 that exposes a small area of the conductive band 59. Each sensor opening 62 is preferably positioned circumferentially about the catheter 22 inline with each of its adjacent ports 40. A corresponding sensor lead 64 is coupled to the conductive band 59 of a respective sensor ring 58, for example, as shown to good advantage in FIG. 8. Each sensor lead 64 exits the wire lumen 70 and protrudes through the exterior wall 56 along the bottom of the catheter 22. Each of the copper wire 66 and constantan wire 68 housed within the sensor lead 64 is electrically connected at a single, common point to the conductive band 59 of the sensor ring 58.

By connecting the copper wire 66 and the constantan wire 68 to the conductive band 59 at a single point, a thermocouple is created. A thermocouple is a device for measuring temperature. In an exemplary embodiment, a T-type thermocouple may be implemented in which a pair of wires of dissimilar metals are joined at one end of the wires and the free ends of the wires are connected to an instrument that measures the difference in potential between the wires. The difference in potential is proportional to the difference in temperature between the joined end and the free ends. The free ends are usually at a known reference temperature. Thus, by creating an interface between a copper wire 66 and constantan wire 68 in the sensor lead 64 at the sensor rings 58, a potential difference can be measured between the copper wire 66 and the constantan wire 68 that can be translated into a temperature reading. It should be noted that other types of thermocouples may also be implemented. In addition, a thermistor could likewise be used instead of a thermocouple for measuring temperature readings on each of the conductive bands.

Therefore, by connecting a sensor lead 64 with a respective sensor ring 58, a thermocouple sensor is created and temperature measurements can be made along the length of the ablation electrode section 20 of the catheter 22 at a series of points between each of the ports 40. This allows a clinician to monitor the temperature of the cardiac tissue being ablated along the length of the linear lesion being created and determine whether an increase in energy application is necessary to reach an optimum temperature for forming lesion, or whether hot spots exist at certain points along the lesion and thus indicate that a reduction in applied energy is warranted. In the embodiment depicted in FIGS. 5-8, it is desirable that the material chosen for the conductive band 59 be both a good thermal and electrical conductor as the interface with the sensor lead 64 is not directly adjacent to the sensor opening 62 in the surface coating 60, which is the location of the thermal and electrical interface with the cardiac tissue.

In addition to functioning as a thermocouple sensor, the sensor rings 58 may also be used as electrocardiograph sensors to monitor the cardiac signals. In this respect, the sensor rings 58 may be used to monitor the electrical impulses of the heart both before, during, and after a lesion in the tissue is formed by the application of ablation energy by the catheter 22. The cardiac signals may be monitored via the transmission along either the copper wire 66 or the constantan wire 68; however, the copper wire 66 is preferred as connection to the copper wire of the electrocardiograph monitor 82 avoids introduction of an unnecessary thermocouple junction. By comparing the transmission of electrical signals by the heart from before treatment with the transmission signatures after treatment, a clinician can determine whether the ablation procedure has been effective.

The purpose of the surface coating 60 on each of the sensor rings 58 is two-fold. First, the surface coating 60 acts as a thermal insulator. By thermally insulating the conductive band 59 except in the area of the sensor opening 62, a more accurate temperature reading at a point along the linear lesion being formed in the cardiac tissue can be made. The conductive band 59 is thermally insulated from the cooling effects of both the blood in the cardiac environment and the conductive fluid being emitted from the ports 40 of the catheter 22. Thus, heat transfer only takes place between the cardiac tissue and the sensor ring 58 at a corresponding sensor opening 62.

The surface coating 60 also electrically insulates each of the sensor rings 58. This is important because were the entire conductive band 59 to be exposed, the energized conductive fluid emitted through the ports 40 of the catheter 22 may also energize the conductive band 59. This is problematic at very high energy levels and areas of blood stasis. If the energy level were high, the blood flow low and the conductive band uncoated it may cause thermal necrosis of blood contacting the conductive band. This coagulum could propagate over the conductive band, potentially clogging the ports and impact the emission of the conductive fluid and the efficacies of the ablation electrode section. Of even more concern is the possibility that a large piece of coagulum could be dislodged from the catheter and potentially cause an embolic event.

Second, without the coating, it may be possible for a ring electrode to create an area of increased current density, possibly overheating cardiac tissue. Also, because of the potential for formation of hot spots along the conductive band, the actual temperature of the conductive band might be higher than the temperature of the adjacent cardiac tissue thus producing a false temperature reading.

As noted above, the position of the sensor rings 58 on the outside surface of the catheter 22 also helps to isolate the sensor opening 62 from direct contact with the conductive fluid emission from the adjacent ports 40. The outer surface of the sensor rings 58 is set-off from the outer surface of the catheter 22 by the thickness of the sensor rings 58. This set-off distance also helps provide for adequate fluid flow out of the ports 40 by ensuring that the cardiac tissue is slightly spaced apart from each of the ports 40 by the thickness of the sensor rings 58.

Figure 9:
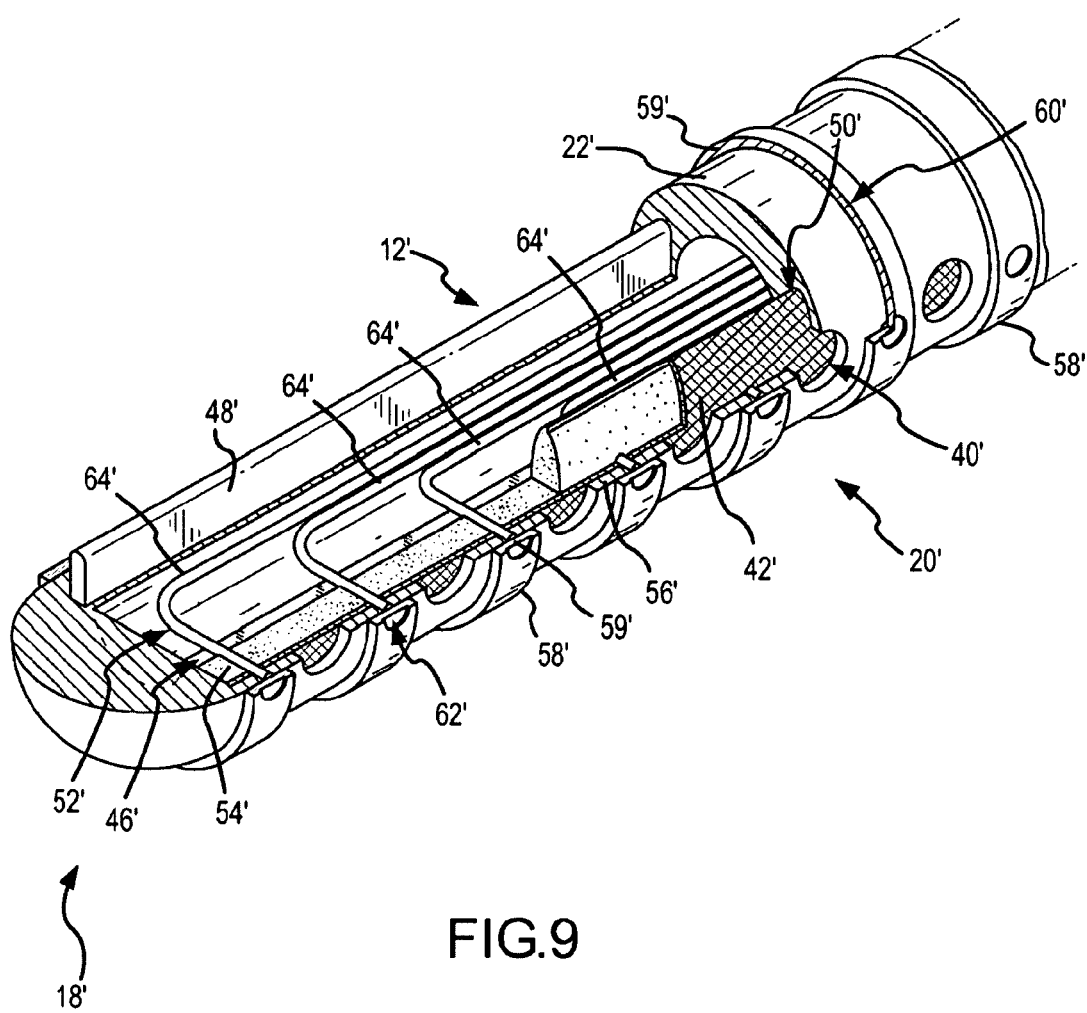
FIG. 9 is an isometric view with a partial cut-away of an alternate embodiment of a catheter according to the present invention.

An alternative embodiment of the ablation electrode section 20' of the catheter 22' is depicted in FIG. 9. The primary difference between this embodiment and the previous embodiment depicted in FIGS. 4-8, is the location of the coupling between the sensor leads 64' and the conductive bands 59' of each of the sensor rings 58'. In this embodiment, each of the sensor leads 64' is housed within the fluid lumen 52'. The distal end of each sensor lead 64' travels through the dispersion opening 46', through the porous material 54', through the mesh material 42', through the exterior wall 56' of the catheter 22', and is electrically connected with the conductive band 59' at a position directly behind a respective sensor opening 62' in the respective sensor ring 58'. The embodiment of FIG. 9 may be preferred in certain circumstances wherein a very sensitive temperature reading is required. By creating the thermocouple at the distal end of the sensor lead 64' positioned opposite the sensor opening 62', any potential effect of heat dissipation through the length of the conductive band 59' is minimized because the temperature reading is taken at the sole point of heat transfer between the cardiac tissue and the sensor ring 58'.

Temperature Discriminator

Figure 10:
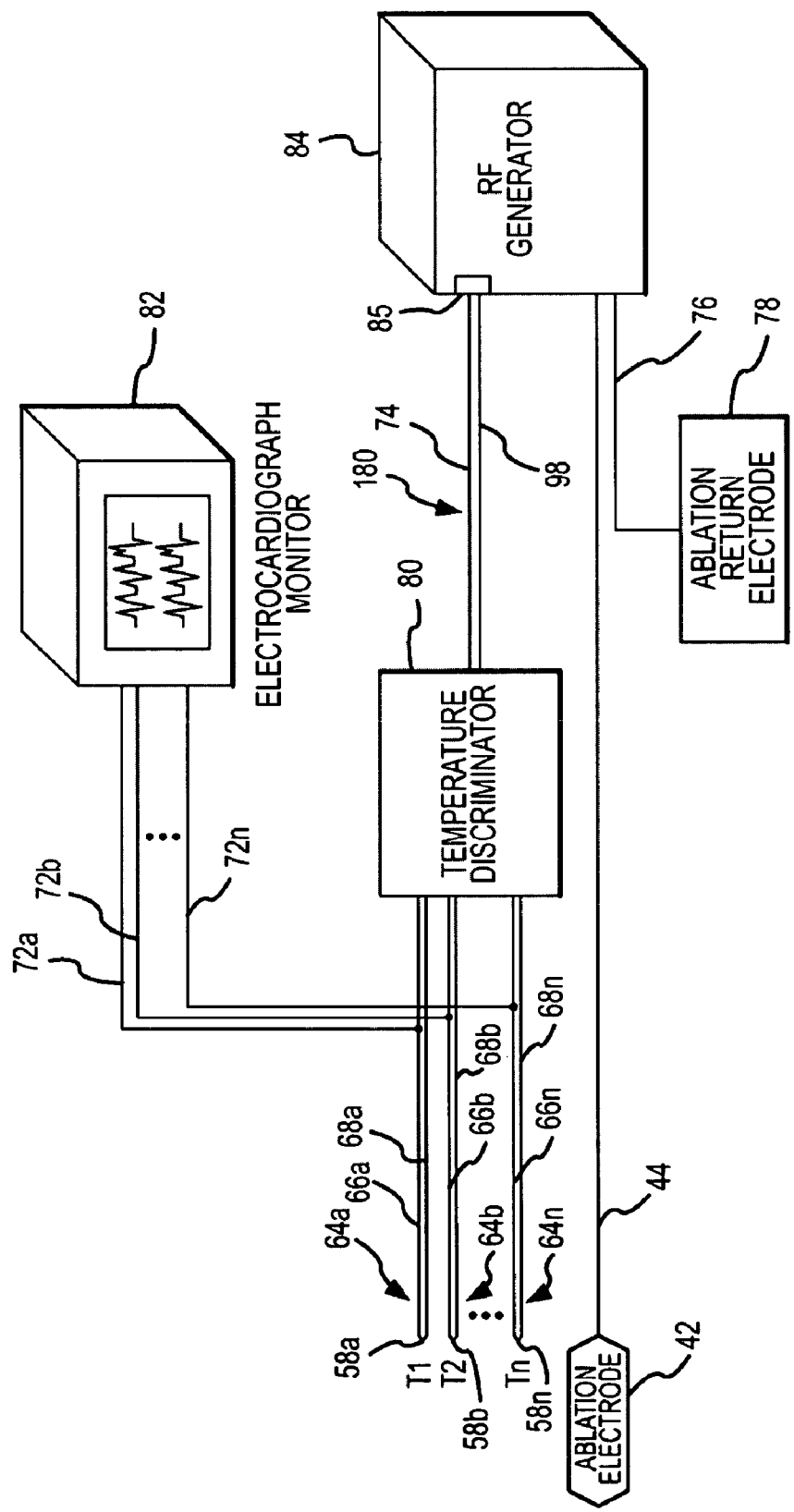
FIG. 10 is a schematic diagram of a thermocouple sensor monitoring system according to a first embodiment of a system for discriminating between a plurality of temperature sensors of the present invention.

In addition to providing a temperature sensing array, such as for use in combination with a traditional or virtual electrode of a cardiac ablation catheter, the present invention contemplates a system for discriminating between various temperature readings of sensors in the array. The temperature discriminating system, for example, may discriminate between the sensor rings 58 described in the virtual electrode above, for example, to determine a high temperature, or to determine a low temperature. A first embodiment of a temperature discriminator system according to the present invention, for example, is depicted in FIG. 10. In this embodiment, a temperature discriminator 80 is interposed between an array of remote thermocouple junction T1, T2, Tn temperature sensors (e.g., located in the ablation electrode section 20 described above) and a temperature feedback input 85 of a radio frequency generator 84. A plurality of sensor leads 64a, 64b, 64n connect the temperature discriminator 80 to the array of thermocouple junction T1, T2, Tn temperature sensors. As with many energy generators used in catheter ablation procedures, the RF generator 84 generally has a single temperature feedback input 85, which allows the RF generator 84 to automatically adjust the power output. This adjustment of energy output based upon feedback helps ensure that the energy output is neither too high and thus overly-damaging to the tissue, or too low and thus insufficient to form an adequate lesion.

A single temperature input into an RF generator may be adequate for use with many ablation catheters, for example, catheters for performing spot ablations with a single electrode. However, when creating a continuous linear lesion with a single application of energy, such as with the virtual electrode structure described above, there is the potential for variations in power density of the energy transferred to the tissue at various points along the length of the linear lesion. Such variations in power density can be manifested in the corresponding temperature of the tissue. Thus, by taking multiple temperature readings along the length of the linear lesion during the ablation process, the risk of too high a temperature at any one location can be minimized.

As noted however, a typical RF generator 84 is not equipped to handle multiple temperature inputs. Thus, the temperature discriminator 80 of the present invention monitors the various temperatures for multiple incoming sensor leads 64 and outputs a single temperature, for example, the highest temperature recorded along the length of the linear lesion, to the RF generator 84 via a temperature output lead 180 via the temperature output lead 180. Temperature output lead 180 is composed of signal conductor 74 and return conductor 98. In the case of a RF generator 84 requiring a type "T" thermocouple temperature sensor, conductor 74 is preferably composed of copper and conductor 98 is preferably composed of constantan. As depicted in FIG. 10, each of the sensor leads 64a, 64b, 64n connects a corresponding sensor ring 58a, 58b, 58n to the temperature discriminator 80. As described above, each of the sensor leads 64a, 64b, 64n is composed of a pair of dissimilar wires forming a thermocouple, one wire, for example, being a copper wire 66a, 66b, 66n and the second wire, for example, being a constantan wire 68a, 68b, 68n. Each copper wire 66a, 66b, 66n is joined at its distal end with the distal end of the corresponding constantan wire 68a, 68b, 68n to form a corresponding type "T" thermocouple junction T1, T2, Tn on a corresponding one of the sensor rings 58a, 58b, 58n. Each thermocouple junction T1, T2, Tn creates a voltage potential proportional to the difference in temperature between the distal end and the proximal end of the copper/constantan wire pairs 64a, 64b, 64n. The proximal end of the copper/constantan wire pairs 64a, 64b, 64n terminate in the temperature discriminator 80. In one embodiment, for example, the temperature discriminator 80 is located ex vivo where the termination point of all copper/constantan wire pairs 64a, 64b, 64n are essentially the same temperature (i.e., isothermal). The temperature discriminator 80 then selects, for example, the highest voltage potential corresponding to the highest temperature of the sensor rings 58a, 58b, 58n and outputs this voltage potential to the temperature feedback input 85 of the RF generator 84 via the temperature output lead 180. By providing the voltage potential corresponding to the highest temperature measurement to the RF generator, the effects of nonuniform power density along the lesion can be mitigated by adjustment of the power output of the RF generator to a level for which the highest power density along the lesion is below a damaging level.

Additionally, as shown in FIG. 10, each of the copper wires 66a, 66b, 66n of the sensor leads 64a, 64b, 64n is coupled to an electrocardiograph ("ECG") monitor 82 via corresponding copper ECG leads 72a, 72b, 72n. This allows each of the sensor rings 58a, 58b, 58n to act as an ECG sensor and tests the efficacy of the linear lesion formed during the ablation procedure in eliminating the patient's arrhythmia.

Figure 11:
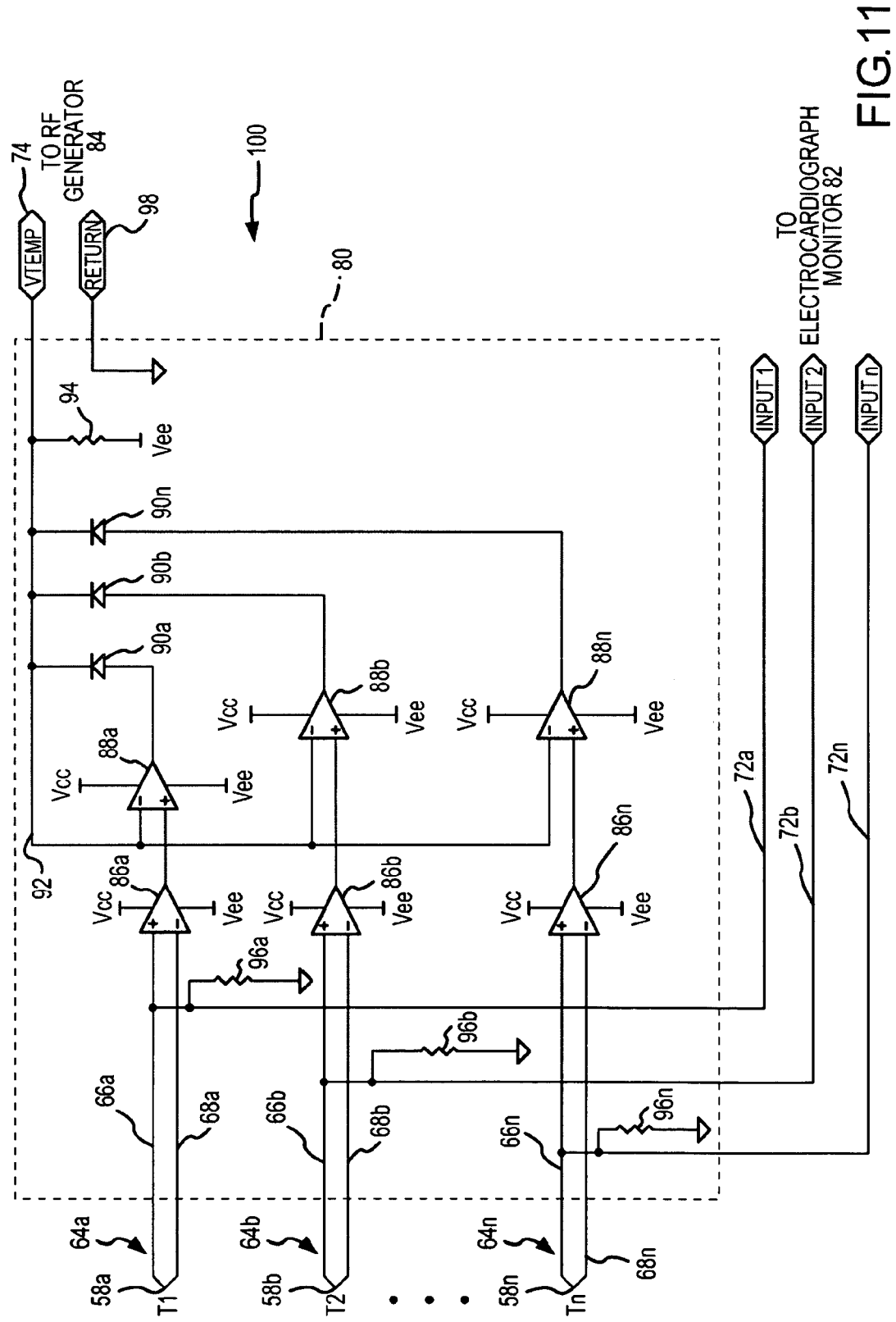
FIG. 11 is a schematic diagram of a first embodiment of a temperature discriminator circuit for use in the thermocouple sensor monitoring system of FIG. 10.

An exemplary circuit 100 performing the function of the temperature discriminator 80 is depicted in FIG. 11. The circuit 100 outputs voltage potential corresponding to the highest temperature of all the temperatures measured at each of the thermocouple junctions T1, T2, Tn. As previously described, each of the sensor leads 64a, 64b, 64n may be formed of a copper wire 66a, 66b, 66n and a constantan wire 68a, 68b, 68n pair with distal ends that are joined together at a corresponding sensor ring 58a, 58b, 58n to create a respective thermocouple junction T1, T2, Tn. As depicted in FIG. 11, the circuit 100 may be expanded to accommodate and discriminate between a plurality of thermocouples and their corresponding temperature inputs. The proximal end of each of the sensor leads 64a, 64b, 64n is connected as an input with the temperature discriminator 80. Each of the copper wires 66a, 66b, 66n is coupled with the positive (noninverting) input of a respective instrument amplifier 86a, 86b, 86n. Similarly, each of the constantan wires 68a, 68b, 68n is coupled with the negative (inverting) input of the corresponding instrument amplifier 86a, 86b, 86n. Each of the copper wires 66a, 66b, 66n may be connected via a respective copper EGG lead 72a, 72b, 72n to the electrocardiograph monitor 82. Each of the copper ECG leads 72a, 72b, 72n is also connected to a local ground via a corresponding high impedance resistor 96a, 96b, 96n. This establishes a reference voltage with a corresponding small bias current for the positive (noninverting) input of the instrument amplifiers 86a, 86b, 86n. The instrument amplifiers 86a, 86b, 86n may provide a gain of unity and are interposed as buffers to isolate the electrocardiogram signals from each other and to provide a low impedance signal input out of the circuit 100. The differential amplifying nature of instrument amplifiers 86a, 86b, 86n also provide for rejection of common mode signals such as the RF ablation signal. The output of each instrument amplifier 86a, 86b, 86n is the input signal for the positive (noninverting) input of a respective, corresponding operational amplifier 88a, 88b, 88n.

The output voltage of each operational amplifier 88a, 88b, 88n is directed to a corresponding diode 90a, 90b, 90n or other appropriate rectifying component. The diodes 90a, 90b, 90n act as a gate and only allow current to flow when the voltage from the output of any one of the respective operational amplifiers 88a, 88b, 88n is sufficiently more positive than the voltage at the feedback loop 92. The circuit 100 also includes a low impedance resistor 94 (e.g., 10 kΩ) coupled between the feedback loop 92 and the negative (inverting) input voltage of Vee of the circuit 100 to drive the output of the operational amplifiers down when the temperatures drop as further explained below. Thus, the output, if any, across each of the diodes 90a, 90b, 90n and the voltage Vee combine to set the voltage on the feedback loop 92, which is the input voltage for the negative (inverting) inputs on each of the operational amplifiers 88a, 88b, 88n.

The voltage on the feedback loop 92 is also the voltage output corresponding to the temperature signal that is sent to the RF generator 84 via the temperature output lead 74. A buffer, such as an optional operational amplifier (not shown) with a gain of unity, may be inserted along the temperature output lead 74 to ensure the strength and stability of the output voltage to the RF generator 84. It should be noted that on most RF generators 84, the expected input is a single thermocouple pair indicating a temperature of the ablating surface. Therefore, the temperature discriminator 80 provides a standard thermocouple potential recognizable by the RF generator 84. It is important that the temperature of the proximal ends of the sensor leads 64a, 64b, 64n be nearly the same as terminals 98 and 74 so as not to introduce any undesired temperature errors due to the inherent introduction of thermocouple junctions within the temperature discriminator 80. This is easily accomplished by constructing and packaging the circuit 100 such that all components are isothermal. The circuit 100 is thus transparent to the RF generator 84 as merely a single temperature input provided to the RF generator 84.

The function of the circuit 100 of the temperature discriminator 80 may be understood via the following simplified example using only two thermocouple inputs T1 and T2. Presume that temperature reading of the cardiac tissue at a thermocouple junction related to input T1 is hot and the temperature reading of the cardiac tissue at a thermocouple junction related to input T2 is less hot than the temperature at thermocouple junction T1. Thus, the voltage input into the first instrument amplifier 86a is greater than the voltage input into the second instrument amplifier 86b. Next, presume for the sake of simplicity that the output of the first instrument amplifier 86a is 1 volt and the output of the second instrument amplifier 86b is 0.5 volts. Thus, 1 volt is input into the noninverting input of the first operational amplifier 88a and 0.5 volts is input into the noninverting input of the second operational amplifier 88b. Again, for the sake of simplicity, presume the voltage of feedback loop 92 is nearly equal to the negative power supply voltage Vee by virtue of the resistor 94. Thus, an initial input voltage to the inverting input of each of the operational amplifiers 88a, 88b that is nearly the power supply voltage of the negative (inverting) input voltage Vee of the operational amplifiers 88a and 88b is provided.

Due to the presence of a more positive voltage on the noninverting inputs and the presence of a more negative voltage on the inverting inputs of both operational amplifiers 88a and 88b, the output of both operational amplifiers 88a and 88b will begin to rise rapidly. The diodes 90a and 90b will correspondingly conduct and the voltage at the feedback loop 92 will rise. As the voltage at the feedback loop 92 reaches 0.5 volts, both the inverting and noninverting inputs of the second operational amplifier 88b are essentially the same and the output of the second operational amplifier 88b stops rising. However, the noninverting input of the first operational amplifier 88a is still more positive than its inverting input, so the output of the first operational amplifier 88a continues to rise, which in turn causes the voltage at the feedback loop 92 to continue to rise. Since the feedback loop 92 is connected to the inverting input of the second operational amplifier 88b and this voltage is now greater than its noninverting input (0.5 volts in this example), the output voltage of the second operational amplifier 88b will fall rapidly. The second diode 90b is now reverse-biased and can no longer influence the voltage at the feedback loop 92. Meanwhile, the output of the first operational amplifier 88a continues to rise until the voltage at the feedback loop 92 (and hence its inverting input) reaches the voltage of the noninverting input (1 volt in this example). The output of the first operational amplifier 88a stops rising as equilibrium has been achieved and the voltage at the feedback loop 92 now equals the higher of the two voltage outputs measured at the instrument amplifiers 86a and 86b.

As a further example, suppose the voltage output of the second instrument amplifier 86b now increases to 1.5 volts (due to an increase in temperature at sensor ring 58b). The noninverting input of the second operational amplifier 88b is now greater than its corresponding inverting input, so the output of the second operational amplifier 88b now begins to rise rapidly. As the output of the second operational amplifier 88b becomes sufficiently positive, the second diode 90b will begin to conduct and the voltage at the feedback loop 92 will begin to rise. The output of the first operational amplifier 88a will fall as its inverting input, which is connected to the feedback loop 92, is more positive than its noninverting input (still 1 volt in this example). The first diode 90a will cease to conduct and the voltage at the feedback loop 92 will increase until equilibrium is achieved with the noninverting input of the second operational amplifier 88b (1.5 volts in this example). Thus, the voltage output from the second instrument amplifier 86b representing the temperature of tissue adjacent sensor ring 58b is equal to the voltage on the feedback loop 92, which in turn is the same as the voltage output to the RF generator 84 from the temperature discriminator 80 via the temperature output lead 74. Understanding that the feedback loop 92 is ultimately driven by the output of the operational amplifier 88a, 88b with the highest input, the circuit 100 will always output a voltage to the RF generator 84 corresponding to the highest temperature measurement of each of the two thermocouple inputs T1, T2.

It should be noted that the circuit 100 is also designed to decrease the output voltage to the RF generator 84 as the highest temperature reading of the thermocouple inputs T1, T2 decreases from a most recent maximum. Assume, for example, that the input voltage at the second operational amplifier 88b suddenly decreases to 1.25 volts while the input voltage at the first operational amplifier 88a remains at 1 volt. The voltage at the feedback loop 92, which was at 1.5 volts, is now more positive than the noninverting input of the second operational amplifier 88b. The output of the first operational amplifier 88a does not change since the inverting input is still more positive than the noninverting input (1.5 volts to 1 volt). However, the output of the second operational amplifier 88b will begin to fall and the second diode 90b will cease conducting. Thus, for the moment, neither the first diode 90a nor the second diode 90b is conducting. However, by coupling the feedback loop 92 with the negative power supply voltage Vee through the resistor 94, the voltage at the feedback loop 92 is reduced to ultimately reach equilibrium with the 1.25 volt potential at the noninverting input of the second operational amplifier 88b, and the second diode 90b again conducts.

Based upon the voltage output from the circuit 100, the RF generator 84 can dynamically adjust the power output to the ablation electrode section of the catheter to optimize the lesion created in the cardiac tissue. For example, if the highest tissue temperature measurement is determined to be greater than 50° C., the RF generator 84 can automatically reduce the power output to ensure that unwanted tissue damage does not occur. Likewise, if the highest temperature measurement is determined to be less than an optimal temperature for tissue ablation, the RF generator 84 can automatically increase the power output to ensure that the tissue is adequately ablated.

Figure 12:
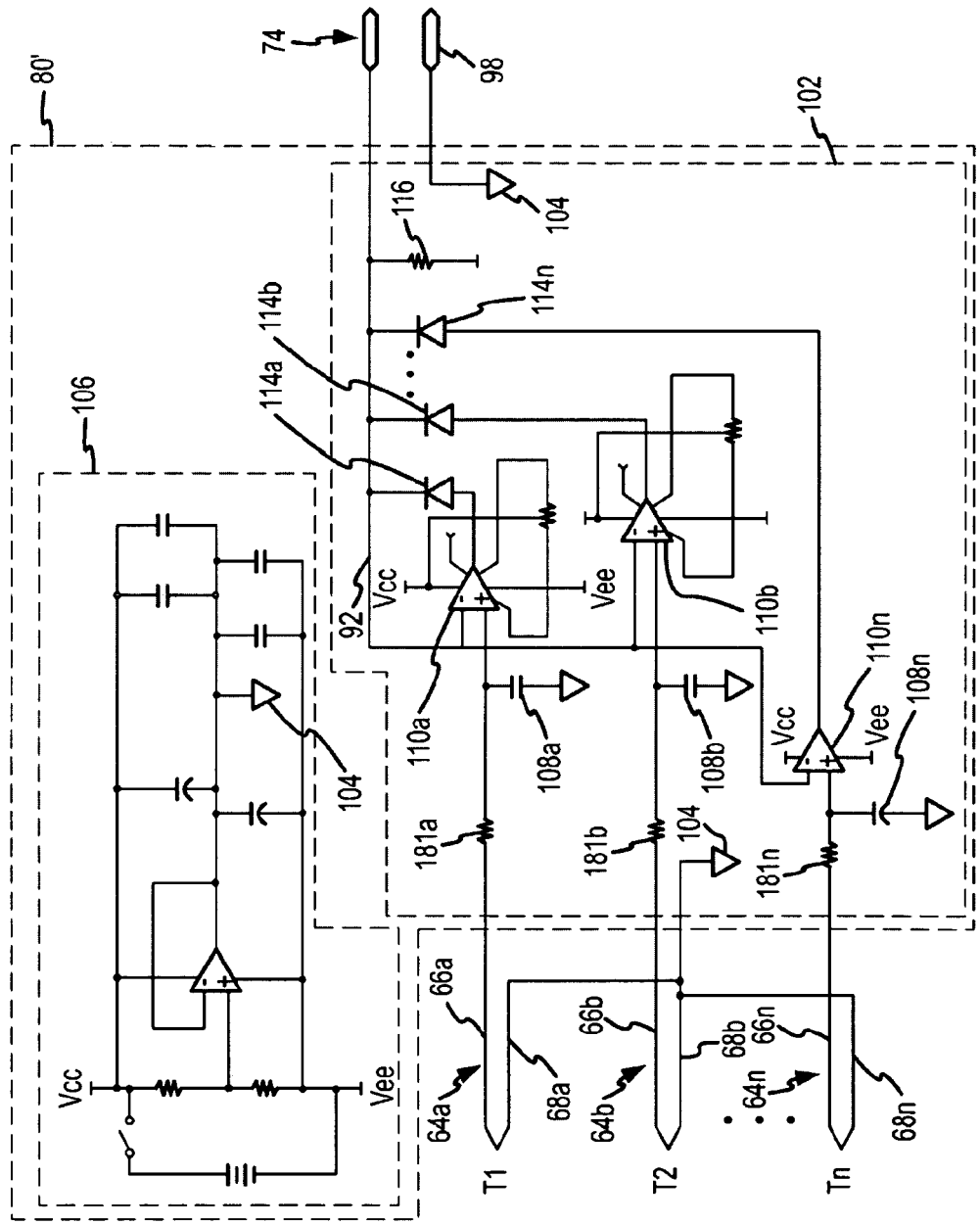
FIG. 12 is a schematic diagram of a second embodiment of a temperature discriminator circuit for use in the thermocouple sensor monitoring system of FIG. 10.

A second embodiment of a circuit 102 that may be used as a temperature discriminator 80' for discriminating between multiple thermocouple temperature sensors is depicted in FIG. 12. The circuit discriminates between the sensors and outputs the highest temperature of all the temperatures measured at each of the thermocouple junctions T1, T2, Tn. As previously described, each of the sensor leads 64a, 64b, 64n may be formed of a copper conductor 66a, 66b, 66n (e.g., a wire, a trace on a printed circuit board, flex circuit, etc.) and a constantan conductor pair 68a, 68b, 68n having their distal ends joined together at a corresponding sensor ring 58a, 58b, 58n to create a respective thermocouple junction T1, T2, Tn. As depicted in FIG. 12, the circuit may be expanded to accommodate and discriminate between any plurality of thermocouples and their corresponding temperature inputs. The proximal ends of each of the copper conductors are connected as inputs with the temperature discriminator 80'. Each of the constantan wires are coupled together in a common constantan return conductor, thus reducing the number of wires or other conductors required within the catheter. This allows for reducing the size of the catheter, which may decrease the trauma afflicted on a patient by the introduction and manipulation of the catheter.

The ground for the temperature discriminator circuit 102 shown in FIG. 12 comprises a pseudo-ground 104 generated by a split power supply circuit 106. The pseudo-ground 104 is used in this embodiment to create a split power supply because the signal received from the copper conductors of the thermocouples is very near ground (e.g., two to three orders of magnitude smaller than the input of a thermistor). By using a pseudo-ground 104 that creates a greater difference between the ground potential of the circuit and the input signals of the thermocouples T1, T2, Tn, the split power supply circuit 106 enables the temperature discriminator 80' to more easily detect and discriminate between the various input signals of the thermocouple T1, T2, Tn inputs. Thus, in the embodiment of FIG. 12, the buffer stage of instrument amplifiers used in the embodiment of FIG. 11 is no longer needed.

At the input to the temperature discriminator 80', resistors 181a, 181b, and 181n, and capacitors 108a, 108b, and 108n, respectively function as a low pass filter for each input to remove high frequency noise from the input signal. In one embodiment, for example, the resistors are 10K ohms and the capacitors are 0.1 microfarads.

The input signal from each copper conductor 66a, 66b, 66n of the thermocouple junctions T1, T2, Tn is also connected to a positive (noninverting) input of an operational amplifier 110a, 110b, 110n. As shown in FIG. 12, the operational amplifiers 110a, 110b, 110n may comprise an operational amplifier with offset trimming potentiometers added. In one configuration, for example, a Linear Technology Corp. model LT1056 JFET input operational amplifier may be used. In another configuration, a chopper stabilized operational amplifier, such as a Linear Technology model LTC1050, can be used without trimming potentiometers. Other known amplifier configurations may also be used.

Negative (inverting) inputs of the operational amplifiers 110a, 110b, 110n provide feedback inputs and are connected to the voltage output 92 of the temperature discriminator circuit 80'.

An output of each of the operational amplifiers 110a, 110b, 110n is connected to an anode of a diode 114a, 114b, 114n, and a cathode of each diode 114a, 114b, 114n is connected to the voltage 92 output of the temperature discriminator circuit 80'. As shown in FIG. 12, each of the diodes 114a, 114b, 114n are arranged so that they will conduct when the output voltage of the operational amplifiers 110a, 110b, 110n is greater than the output voltage by at least a forward-bias voltage level of the diode as described above with respect to FIG. 11.

As described above with respect to the thermocouple circuit 100 shown in FIG. 11, it is also important for the proximal ends of sensor leads 64a, 64b, 64n, and the output voltage nodes 74 and 98 be at the same temperature (i.e., isothermal) so that no errors are introduced by the transition from the thermocouple conductors to other metals in the circuit or from the thermal energy of the components. Since the circuit generates little heat, isothermal conditions may be achieved through the use of proper packaging, layout, and heat-sinking.

The operation of the temperature discriminator circuit 102 may also be understood via the simplified example described with reference to FIG. 11 above for the two thermocouple inputs T1 and T2.

The temperature discriminator circuit 80' shown in FIG. 12 can be altered to discriminate the lowest temperature instead of the highest temperature sensed at the thermocouple junctions T1, T2, Tn. The circuit 80' is modified by reversing the direction of the diodes 114a, 114b, 114n and by changing the load resistor 116 to a pull-up load resistor configuration instead of the pull-down configuration shown in FIG. 12.

Figure 13:
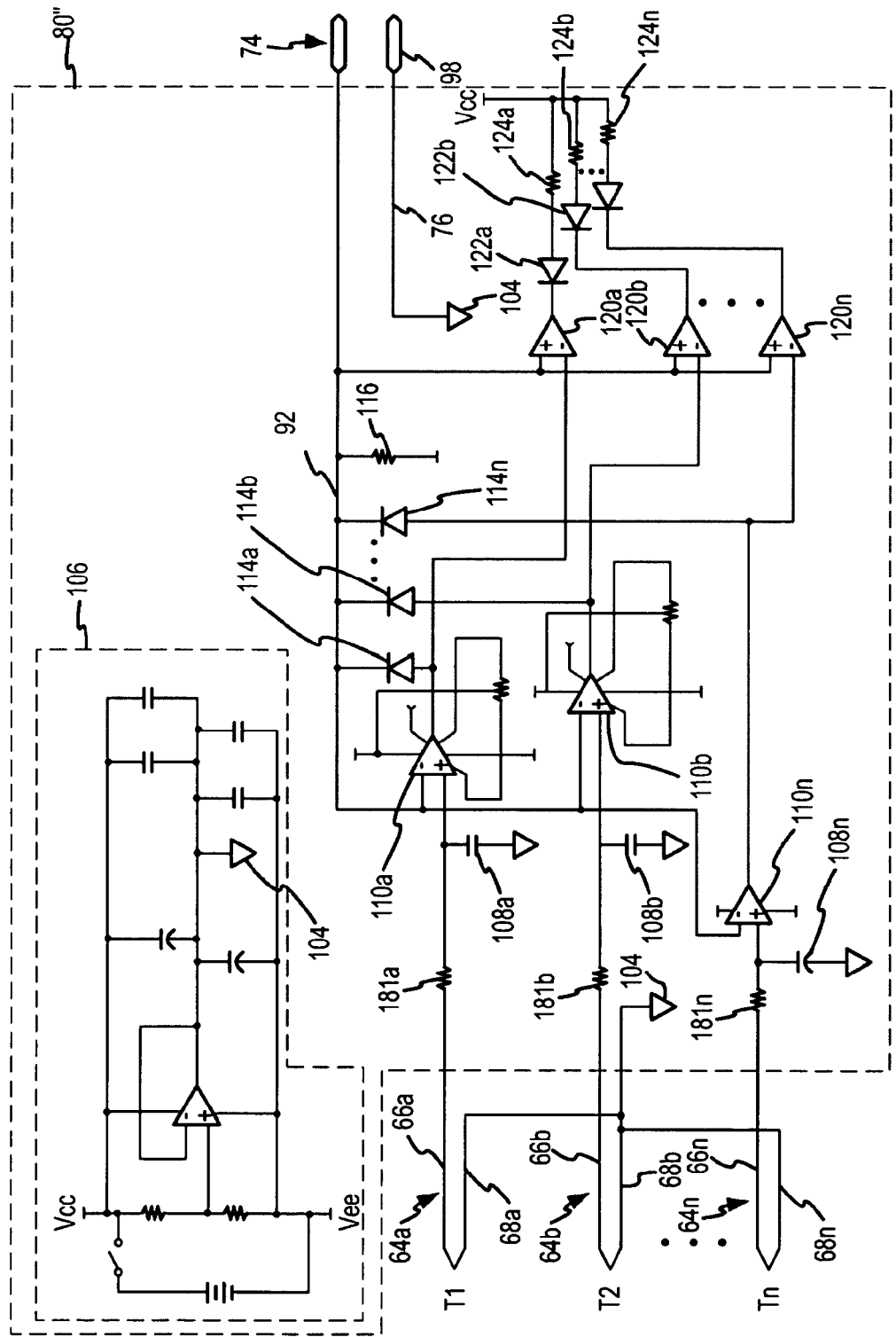
FIG. 13 is a schematic diagram of a third embodiment of a temperature discriminator circuit for use in the thermocouple sensor monitoring system of FIG. 10.

FIG. 13 is a schematic diagram of a third embodiment of a circuit 118 that may be used as temperature discriminator circuit 80" for discriminating between multiple thermocouple junctions T1, T2, Tn located at the sensor rings 58a, 58b, 58n of an ablation catheter according to the present invention. The temperature discriminator circuit 80" includes the same discriminatory circuitry as the embodiment of the temperature discriminator 80' shown in FIG. 12, but further comprises comparators 120a, 120b, 120n and indicators, such as light emitting diode (LED) indicators 122a, 122b, 122n, that may be used to provide feedback to an operator of the ablation catheter. Where the components are the same, those components are labeled with the same reference numbers shown in FIG. 12 and are not described further. The indicators may, for example, provide a visual indication showing which thermocouple temperature sensor is the hottest (or coldest). Alternatively, the indicators may provide an indication of which temperature sensors are above or below a threshold temperature level. The indicators may also provide other types of indications, such as audible or tactile indications.

In this embodiment, each output of the operational amplifiers 110a, 110b, 110n is connected to one of the diodes 114a, 114b, 114n respectively, as described above with respect to FIG. 12 and is also connected to a negative (inverting) input of one of the group of comparators 120a, 120b, 120n. The output voltage 92 of the temperature discriminator circuit is connected to a positive (non-inverting) input of the comparators 120a, 120b, and 120n. The comparators are also connected to the voltage source Vcc and Vee. Each output of the comparators 120a, 120b, 120n is connected to a cathode of one of the LEDs 122a, 122b, 122n, respectively. An anode of each LED 122a, 122b, and 122n is connected to the voltage supply Vcc via a resistor 124a, 124b, 124n.

In operation, output voltage 92 is slightly lower than one of the outputs of the operational amplifiers 110a, 110b, 110n by one diode. One of the operational amplifiers (e.g., op amp 110a) has an output voltage that is one forward diode drop higher than the output voltage 92. This is the operational amplifiers corresponding to the thermocouple with the highest temperature. All other operational amplifiers have a low voltage output, approaching the negative supply Vee. As the output of the operational amplifier (e.g., op amp 110a) is higher than output voltage 92, the corresponding comparator (e.g., comparator 120a) has its negative (inverting) input higher than its positive (non-inverting) input, and as such, the output of that comparator (e.g., comparator 120a) is driven low, approaching Vee. This provides a current path allowing forward bias for the corresponding LED (e.g., LED 122a) and thus illuminates this LED (e.g., LED 122a). All other comparators (e.g., comparators 120b, 120n) have their negative (inverting) inputs low, near Vee, while the positive (non-inverting) input is at output voltage 92. Output voltage 92 is always more positive than Vee by a wide margin, and as such, these comparators always have their inverting inputs more negative than the non-inverting inputs. Said comparators thus drive their outputs in the positive direction toward Vcc, and as such, do not provide a conductive path for the other LEDs (e.g., LEDs 122b, 122n) and said LEDs (e.g., LEDs 122b, 122n) do not illuminate. Thus, the LED corresponding to the thermocouple having the highest sensed temperature is illuminated, and the remaining LEDs remain off.

Figure 14:
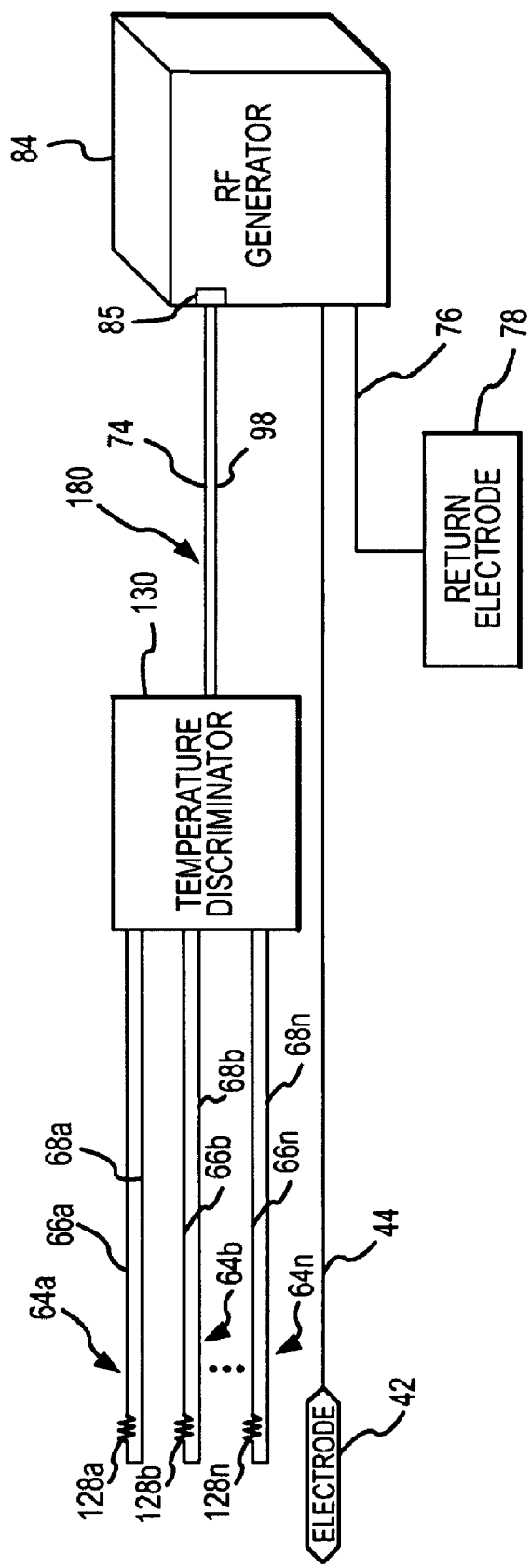
FIG. 14 is a schematic diagram of a thermistor sensor monitoring system according to a second embodiment of a system for discriminating between a plurality of temperature sensors of the present invention.

FIG. 14 is a schematic diagram of a thermistor sensor monitoring system 126 according to the present invention. The thermistor sensor monitoring system 126 is similar to the thermocouple sensor monitoring system shown in FIG. 10, but includes thermistor temperature sensors instead of the thermocouple temperature sensors shown in FIG. 10. Where the same components are shown in FIG. 14 as are shown and described with reference to FIG. 10, reference numbers remain the same and are not discussed in further detail with respect to FIG. 14. It is noted, however, that conductors 66a, 66b, 66n and 68a, 68b, 68n used for a thermistor are typically both copper.

The thermistor sensor monitoring system 126 comprises a plurality of thermistor temperature sensors 128a, 128b, 128n connected to a temperature discriminator circuit 130. As described above with respect to FIG. 10, the temperature discriminator circuit 130 receives the inputs from the plurality of thermistor temperature sensors 128a, 128b, 128n and provides a single output to the temperature feedback input 85 of the RF generator 84 via the temperature output lead 74. The single output may comprise, for example, a voltage corresponding to the highest temperature sensed at the plurality of thermistor temperature sensors 128a, 128b, 128n, or the lowest temperature sensed at the plurality of thermistor temperature sensors.

Figure 15:
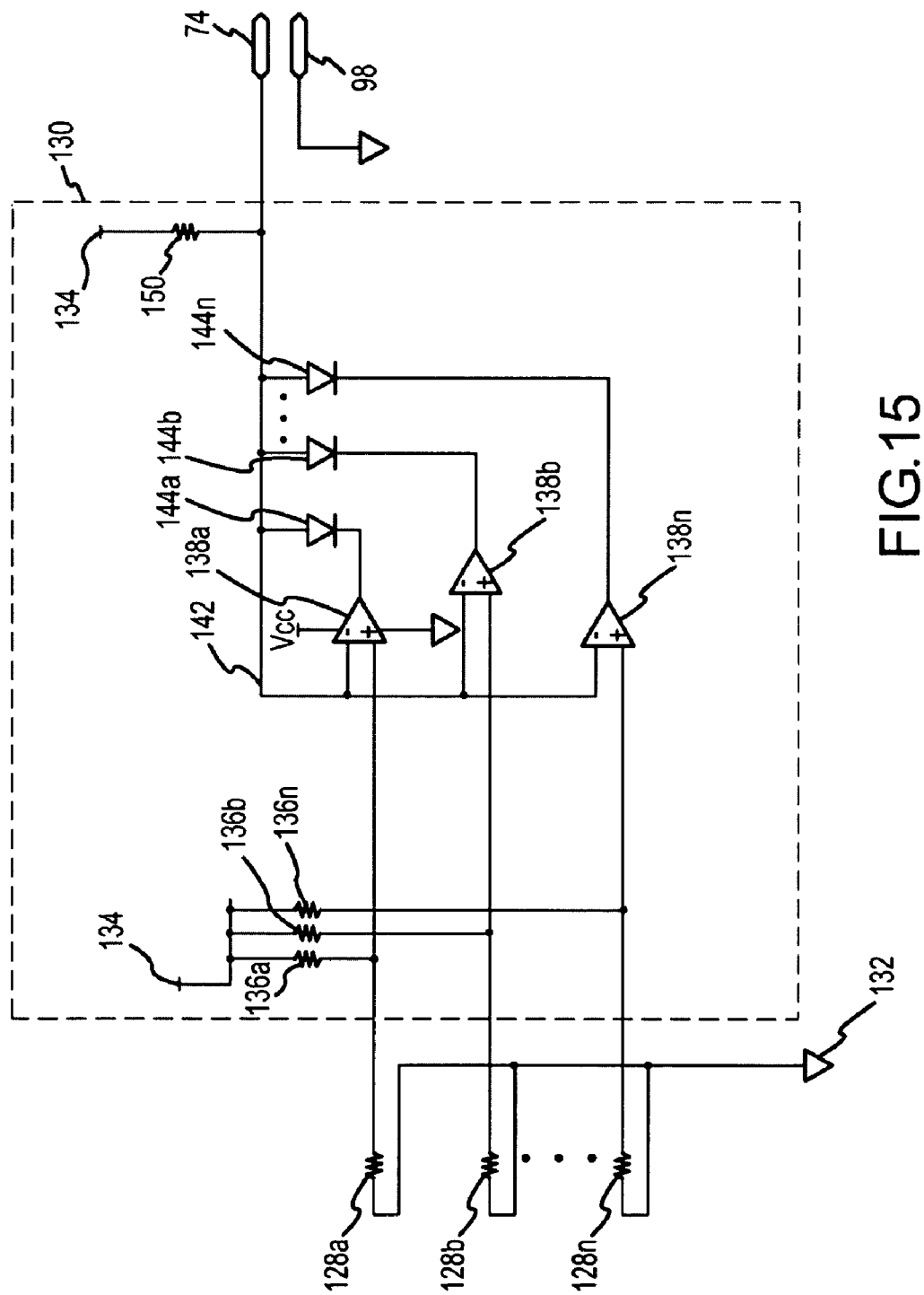
FIG. 15 is a schematic diagram of a first embodiment of a temperature discriminator circuit for use in the thermistor sensor monitoring system of FIG. 14.

FIG. 15 is a schematic diagram of a first embodiment of a thermistor temperature discriminator circuit 130 for discriminating between the plurality of thermistor temperature sensors 128a, 128b, 128n shown in FIG. 14. In this embodiment, the thermistor temperature sensors 128a, 128b, 128n are connected between ground 132 and the temperature discriminator circuit 130 and are located at the sensor rings 58a, 58b, 58n as described above with respect to FIG. 8. Each of the thermistor temperature sensors 128a, 128b, 128n are also connected to a reference voltage 134 via a respective pull-up resistor 136a, 136b, 136n. The reference voltage may, for example, be matched to a reference voltage used by the RF generator 84 to identify a single input voltage, such as approximately 1.235 volts, or another appropriate reference voltage. Each of the thermistor temperature sensors 128a, 128b, 128n are further connected to a positive (noninverting) input of an operational amplifier 138a, 138b, 138n of the temperature discriminator circuit 130, respectively. The negative (inverting) inputs of the operational amplifiers 138a, 138b, 138n are connected to the output voltage 140 of the temperature discriminator circuit 130 via a feedback control loop 142. The operational amplifiers are also connected to the voltage supply Vcc and the circuit ground 132 as shown in FIG. 15. Each output of the operational amplifiers 138a, 138b, 138n is connected to a cathode of a respective diode 144a, 144b, 144n, and an anode of the diode 144a, 144b, 144n is connected to the output voltage 142 of the temperature discriminator circuit 130. Each of the diodes 144a, 144b, 144n is thus forward-biased when the output voltage 142 of the temperature discriminator circuit 130 is greater than the output voltage of the respective operational amplifier 138a, 138b, 138n by at least the threshold voltage of the diode 144a, 144b, 144n. The output voltage 142 of the temperature discriminator circuit 130 is also connected to the voltage supply Vcc via a pull-up resistor 146. A return signal 98 is connected to the ground 104 to complete the circuit.

The operational amplifiers 138a, 138b, 138n and diodes 144a, 144b, 144n of the temperature discriminator circuit 130 are configured as a precision clamp circuit. The operational amplifier is configured as a unity gain follower, but with the diode in the feedback loop. The diode 144a, 144b, 144n allows the operational amplifier 138a, 138b, 138n to pull the overall output voltage 142 to a lower value, but does not allow the operational amplifier 138a, 138b, 138n to push the overall output voltage 142 to a higher value because when the output voltage of the operational amplifier 138a, 138b, 138n is higher than the output voltage 142 of the temperature discriminator circuit 130 the diode 144a, 144b, 144n is reverse-biased and does not allow current to flow through the diode. The plurality of operational amplifiers 138a, 138b, 138n and diodes 144a, 144b, 144n are connected in parallel, and whichever operational amplifier and diode are connected to the lowest voltage (i.e., the highest temperature) will dominate and draw the output, voltage 142 of the temperature discriminator circuit 130 to the voltage of the corresponding thermistor temperature sensor 128a, 128b, 128n.

The operation of the temperature discriminator circuit 130 can be understood via the following example. Assuming that the temperature at the first thermistor temperature sensor 128a is 50° C., the temperature at the second thermistor temperature sensor 128b is 55° C., their corresponding voltages at the positive (noninverting) input of their corresponding operational amplifiers 138a and 138b, respectively, are 0.875 volts for the first thermistor temperature sensor 128a and 0.831 volts for the second thermistor temperature sensor 128b respectively, and that the overall output voltage 142 of the temperature discriminator circuit 130 is initially 1.235 volts due to the pull-up load resistor 150. The output of the first operational amplifier 138a will be drawn low until the feedback from the output voltage 142 is drawn down to match the voltage at its positive (noninverting) input, 0.875 volts from the first thermistor temperature sensor 128a. The output of the second operational amplifier 138b will also be drawn low until the feedback from the output voltage 142 is drawn down to match the voltage at its positive (noninverting) input, 0.831 volts from the second thermistor temperature sensor 128b. Since the negative (inverting) inputs to the first and second operational amplifiers 138a, 138b are common, the first operational amplifier 138a at that point has an input voltage at its negative (inverting) input (0.831 volts) that is less than the input voltage at its positive (noninverting) input (0.875 volts). The output voltage of the first operational amplifier 138a is then increased to attempt to bring the voltage level at its negative (inverting) input voltage back to the voltage level at its positive (noninverting) input. The increased output voltage of the first operational amplifier 138a, however, reverse-biases the diode 144a and prevents the output voltage 140 of the temperature discriminator circuit 130 from being drawn down by the first operational amplifier 138a. Thus, the first operational amplifier 138a does not affect the output voltage 142 of the temperature discriminator circuit 130 and the second operational amplifier 138b controls the output voltage 141 to match the input voltage from the second thermistor temperature sensor 128b, i.e., 0.831 volts. The RF generator 84 then receives an input voltage of 0.831 volts, which is the same input voltage as if the RF generator 84 were directly connected to a single thermistor temperature sensor at a temperature of 55° C.

Figure 16:
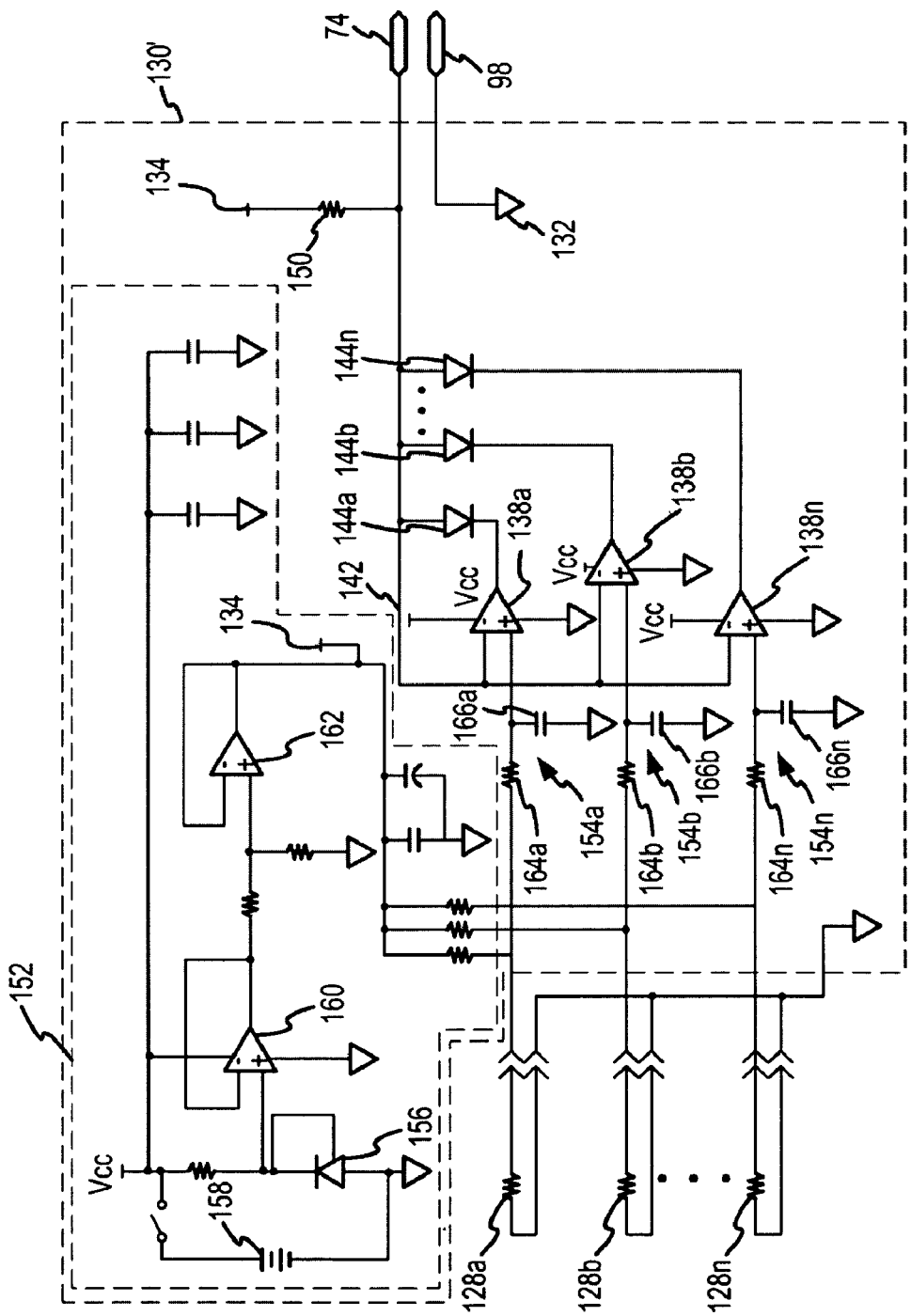
FIG. 16 is a schematic diagram of a second embodiment of a temperature discriminator circuit for use in the thermistors sensor monitoring system of FIG. 14.

FIG. 16 is a schematic diagram of a second embodiment of a thermistor temperature discriminator circuit 130' for discriminating between the plurality of thermistor temperature sensors 128a, 128b, 128n shown in FIG. 14. The thermistor temperature discriminator circuit 130' shown in FIG. 16 is similar to the thermistor temperature discriminator circuit 130 described above with reference to FIG. 15, but further includes a precision voltage reference circuit 152 for stabilizing the reference voltage of the discriminator circuit 130' and further includes an R-C low pass filter 154a, 154b, 154n interposed between the thermistors 128a, 128b, 128n and the inputs to the operational amplifiers 138a, 138b, 138n, respectively. The precision voltage reference circuit 152 includes a voltage regulator diode 156 for regulating the input voltage provided by a battery 158 or other voltage source. The voltage reference diode 156, for example, may comprise a voltage reference level that is the same as the voltage reference level used in the RF generator 84 to analyze a single temperature feedback input signal. The precision voltage reference circuit 152 also includes a pair of operational amplifiers 160, 162 that provide a buffer and additional current drive to the voltage reference provided to the temperature discriminator circuit 130'. The precision voltage reference circuit 152 shown in FIG. 16, however, is merely an exemplary voltage reference circuit that may be used in conjunction with a temperature discriminator circuit, and one skilled in the art could substitute other voltage reference circuits within the scope of the present invention. The R-C low pass filters 154a, 154b, 154n are used to trap high frequency noise. In one embodiment, for example, a resistor 164 having a 10 K ohm resistance value and a capacitor 166 having a 0.1 uF capacitance would provide a cutoff frequency of about 160 Hz. Other component selections could be substituted depending on the desired cutoff value as would be readily appreciated by one skilled in the art. For example, the resistance and/or capacitance could be increased to lower the cutoff frequency such as to filter 60 Hz AC Sine noise. The temperature discriminator circuit 130' otherwise functions the same as the temperature discriminator circuit 130 shown in FIG. 15.

Figure 17:
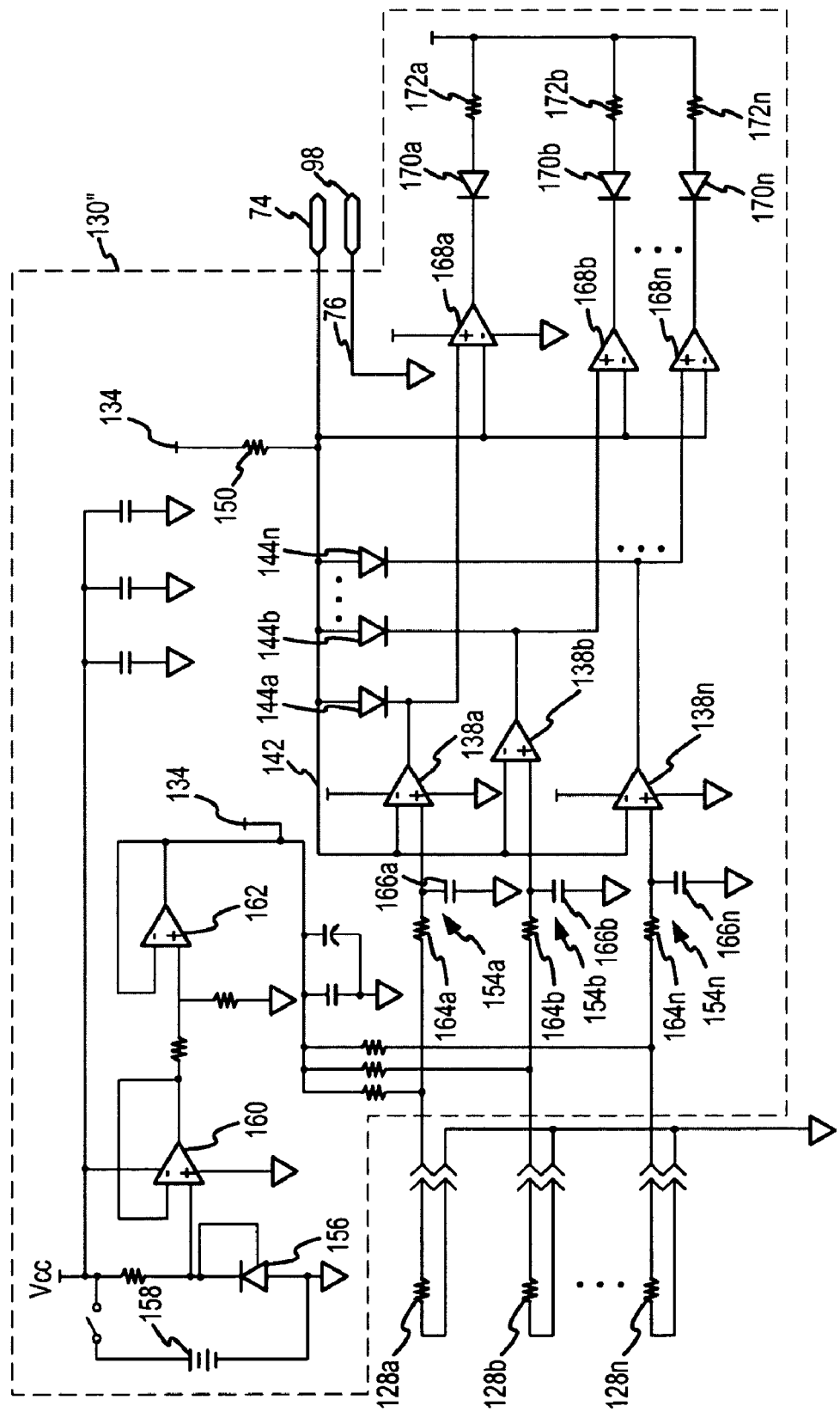
FIG. 17 is a schematic diagram of a third embodiment of a temperature discriminator circuit for use in the thermistors sensor monitoring system of FIG. 14.

FIG. 17 shows a third embodiment of a thermistor temperature discriminator circuit 130" for discriminating between the plurality of thermistor temperature sensors 128a, 128b, 128n shown in FIG. 14. In this embodiment, the temperature discriminator circuit 130" includes the same discriminating circuitry as the embodiment of the temperature discriminator circuit 130', shown in FIG. 16, but further comprises comparators 168a, 168b, 168n and indicators, such as LED indicators 170a, 170b, 170n, to provide feedback to an operator of the ablation catheter. As described above, the indicators may, for example, provide a visual indication showing which thermistor temperature sensor 128a, 128b, 128n is the hottest. Alternatively, the indicators may provide an indication of which temperature sensors are above or below a threshold temperature level. The indicators may also provide other types of indications, such as audible or tactile indications. As shown in FIG. 17, the temperature discriminator circuit 130" has similar components to and operates similarly to the circuit 130' shown in FIG. 16. Where the components are the same, those components are labeled with the same reference numbers shown in FIG. 16 and are not described further.

In this embodiment, each output the operational amplifiers 138a, 138b, 138n is connected to a cathode of the diodes 144a, 144b, 144n, respectively, as described above with respect to FIG. 16 and is also connected to a positive (noninverting) input of one of a plurality of comparators 168a, 168b, 168n. The output voltage 142 of the temperature discriminator circuit 130" is connected to the negative (inverting) input, of each operational amplifier and is further connected to negative (inverting) inputs of the comparators 168a, 168b, 168n. The comparators are also connected to the voltage source Vcc and the ground 132 as shown. The outputs of the comparators 168a, 168b, 168n are connected to the cathode of a plurality of LEDs 170a, 170b, 170n, respectively. The anode of each LED 170a, 170b, 170n is connected to the voltage supply Vcc via a resistor 172a, 172b, 172n, respectively.

In operation, as the temperature discriminator circuit 130" identifies the highest temperature being sensed at the thermistor temperature sensors 128a, 128b, 128n, the output voltage 142 of the temperature discriminator circuit follows the lowest voltage (i.e., the voltage corresponding to the highest temperature) supplied from the individual thermistor temperature sensors 128a, 128b, 128n of the thermistor temperature sensor sensing the highest temperature. This output voltage 142 is then compared to the outputs of the individual operational amplifiers 138a, 138b, 138n via the comparators 168a, 168b, 168n. The output voltage 142 is one diode drop higher than the output of an individual operational amplifier (e.g., op amp 138a) corresponding to the respective individual thermistor (e.g., thermistor 128a) with the lowest output (highest temperature). The corresponding comparator (e.g., comparator 168a) has its negative (inverting) input more positive than its positive (non-inverting) input, and as such, drives its output low, allowing for a forward bias path for the corresponding LED (e.g., LED 170a) and illuminating said LED (e.g., LED 170a). All other operational amplifiers (e.g., LEDs 170b, 170n) have voltage outputs near the positive supply voltage Vcc, and as such, all corresponding comparators (e.g., comparators 168b, 168n) have their positive inputs more positive than their negative inputs. Said comparators (e.g., comparators 168b, 168n) thus drive their outputs in the positive direction towards Vcc, and as such, do not provide a conductive path for the corresponding LEDs (e.g., LEDs 170b, 170n) and said LEDs (e.g., LEDs 170b, 170n) do not illuminate. Thus, the LED corresponding to the thermocouple having the highest sensed temperature is illuminated and the remaining LEDs remain off.

Figure 18:
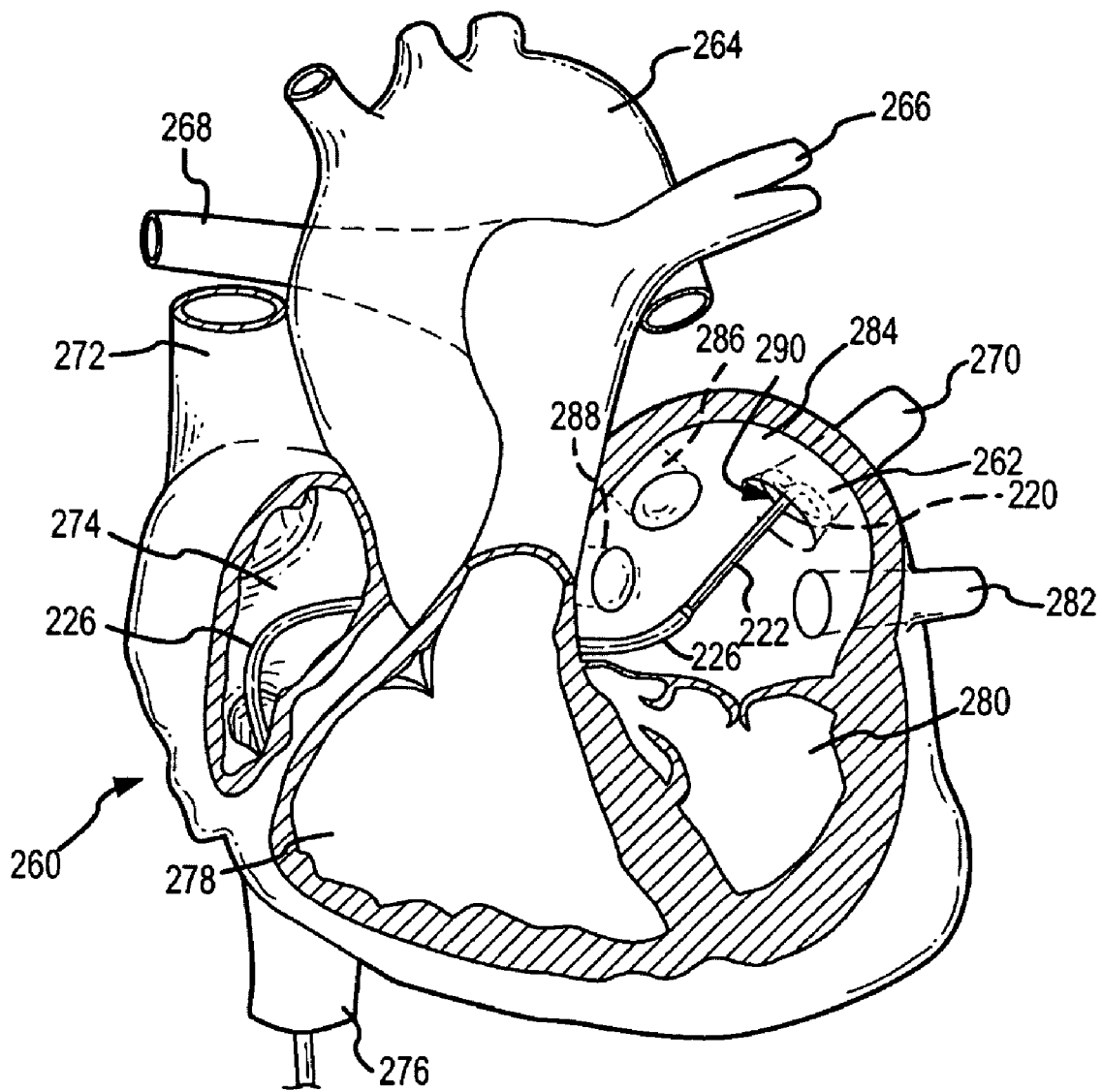
FIG. 18 is an isometric view of a heart with portions of the atria and ventricles cut-away to reveal positioning of a generic version of the catheter of the present invention in the left atrium, adjacent to the left superior pulmonary vein.

FIG. 18 schematically depicts the catheter 222 and ablation electrode section 220 according to a generic embodiment of the present invention being used to ablate tissue in a left superior pulmonary vein 270. FIG. 18 includes a number of primary components of the heart 260 to orient the reader. In particular, starting in the upper left-hand portion of FIG. 18, and working around the periphery of the heart 260 in a counterclockwise fashion, the following parts of the heart 260 are depicted: the superior vena cava 272, the right atrium 274, the inferior vena cava 276, the right ventricle 278, the left ventricle 280, the left inferior pulmonary vein 282, left superior pulmonary vein 270, the left atrium 284, the right superior pulmonary vein 286, the right inferior pulmonary vein 288, the left pulmonary artery 266, the arch of the aorta 264, and the right pulmonary artery 268.

The distal end of the ablation electrode section 220 is positioned adjacent to the ostium 290 of the left superior pulmonary vein 270 using known procedures. For example, to place the ablation electrode section 220 in the position shown in FIG. 18, the right venous system may be first accessed using the "Seldinger technique." In this technique, a peripheral vein (such as a femoral vein) is first punctured with a needle and the puncture wound is dilated with a dilator to a size sufficient to accommodate an introducer, e.g., the outer guiding portion of introducer 226. The outer guiding portion of introducer 226 with at least one hemostatic valve is seated within the dilated puncture wound while maintaining relative hemostasis. From there, the outer guiding portion of introducer 226 is advanced along the peripheral vein, into the inferior vena cava 276, and into the right atrium 274. A transeptal sheath may be further advanced through the outer guiding portion of introducer 226 to create a hole in the interatrial septum between the right atrium 274 and the left atrium 284.

Once the outer guiding portion of introducer 226 is in place in the right atrium 274, the inner guiding portion of introducer 226, housing the catheter 222 with the ablation electrode section 220 on the distal end, is introduced through the hemostatic valve of the outer guiding portion of introducer 226 and navigated into the right atrium 274, through the hole in the interatrial septum, and into the left atrium 284. Once the inner guiding portion of introducer 226 is in the left atrium 284, the ablation electrode section 220 of the catheter 222 and may be advanced through the distal tip of the inner guiding portion of introducer 226. The ablation electrode section 220 as shown in FIG. 18 is being inserted info the ostium 290 of the left superior pulmonary vein 270 to contact the tissue of the walls of the vein. The configuration of the ablation electrode section 220, for example, in a shape as depicted in FIGS. 2 and 3, is advantageous for maintaining consistent contact with tissue in a generally cylindrical vessel. Other configurations of the ablation electrode section 220 may be used to greater advantage on tissue surfaces of other shapes.

While the ablation electrode 220 is in the left superior pulmonary vein 270, the ablation electrode section 220 may be energized to create the desired lesion in the left superior pulmonary vein 270. The RF energy emanating from the ablation electrode section 220 is transmitted through the conductive fluid medium, which flows through the fluid lumen, through the dispersion opening, through the porous material, through the mesh layer, exits the ports, and impacts the adjacent tissue. Thus, a lesion is formed in the tissue by the RF energy. The conductive fluid medium may also experience ohmic heating as it flows along either the electrode lead or through the mesh layer acting as the electrode (depending upon the particular embodiment). Lesion formation may thus also be facilitated by the conductive fluid medium, which may have been heated by ohmic heating to a sufficiently high temperature to facilitate or enhance lesion formation. The RF energy is conducted into the adjacent tissue and the heated conductive fluid convectively affects the temperature of the tissue. In order to form a sufficient lesion, it is desirable to raise the temperature of the tissue to at least 50° C. for an appropriate length of time (e.g., one minute). Thus, sufficient RF energy must he supplied to the electrode to produce this lesion-forming temperature in the adjacent tissue for the desired duration.

While the lesion is being formed, the sensor rings on each side of each of the ports may be simultaneously placed in contact with the cardiac tissue in order to take temperature readings. The thermocouples on each of the sensor rings transmit temperature information to the temperature discriminator unit. The circuit in the temperature discriminator determines the highest temperature measured by any of the sensor rings and outputs this temperature reading to the RF generator. The output power of the RF generator can then be automatically adjusted in real-time to both ensure that an adequate temperature for tissue ablation is being achieved and that the tissue temperature at any point along the lesion does not exceed a maximum threshold that could result in undesirable tissue damage.

Once the lesion is formed, the sensor rings can alternatively monitor the cardiac signals across the lesion to determine whether the ablation procedure achieved the desired effect. The copper wires in the sensor leads are additionally coupled with an electrocardiograph monitor to allow a clinician to analyze the strength and location of cardiac electrical signals. If stray signals are appropriately blocked by the lesion, the arrhythmic condition in the patient should be corrected and reflected in the ECG.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. A circuit for discriminating between a plurality of temperature measurements generated by an array of sensors positioned on an ablation catheter, the circuit comprising:
    an input signal receiving component for receiving a plurality of input signals from individual sensors in the sensor array corresponding to the plurality of temperature measurements;
    a plurality of amplifier components, each having a first input, a second input, and an output, wherein said first input of each amplifier component is coupled with said input signal receiving component for receiving a respective one of the plurality of input signals;
    a plurality of rectifier components, each having a first terminal and a second terminal; wherein said first terminal of each rectifier component is coupled with said output of a respective one of said plurality of amplifier components;
    a single feedback loop coupled with said second terminal of all of said plurality of rectifier components and further coupled with said second input of all of said plurality of amplifier components; wherein the voltage level of said feedback loop substantially follows a voltage received at one of said plurality of said input signal receiving components; and
    an output component coupled with said feedback loop for providing an output signal corresponding to said voltage level of said feedback loop.

2. The circuit of claim 1, wherein an output buffer component is interposed between said feedback loop and said output component.

3. The circuit of claim 1, wherein said input signal receiving component receives the plurality of input signals from an array of thermocouple sensors.

4. The circuit of claim 1, wherein said input signal receiving component receives the plurality of input signals from an array of thermistor sensors.

5. The circuit of claim 1, further comprising a plurality of signal buffer components interposed between the input signal receiving component and the plurality of amplifier components, wherein each signal buffer component is coupled with the first input of a respective one of the amplifier components.

6. The circuit of claim 1, wherein the circuit further comprises a plurality of output leads coupled with the signal receiving component for providing each of the plurality of input signals to an electrocardiograph.

7. The circuit of claim 1, wherein the voltage received at said one of said plurality of said input receiving components corresponds to a high temperature measurement of the plurality of temperature measurements represented by the plurality of input signals.

8. The circuit of claim 1, wherein the voltage received at said one of said plurality of said input receiving components corresponds to a low temperature measurement of the plurality of temperature measurements represented by the plurality of input signals.

9. The circuit of claim 1, wherein any output across each of the rectifier components and a voltage Vee on each of the amplifier components combine to set a voltage on the feedback loop.

10. The circuit of claim 9, wherein the voltage on the feedback loop is an input voltage for inverting inputs on each of the amplifier components.

11. A circuit for discriminating between a plurality of temperature measurements generated by an array of sensors positioned on an ablation catheter, the circuit comprising:

an input signal receiving component communicatively coupled to individual sensors in the sensor array, the input signal receiving component receiving a plurality of input signals from the individual sensors corresponding to the plurality of temperature measurements;

a plurality of amplifier components, each having a first input, a second input, and an output, wherein said first input of each amplifier component is coupled with said input signal receiving component to receive a respective one of the plurality of input signals;

a plurality of rectifier components, each having a first terminal and a second terminal; wherein said first terminal of each rectifier component is coupled with said output of a respective one of said plurality of amplifier components;

a single feedback loop coupled with said second terminal of all of said plurality of rectifier components and further coupled with said second input of all of said plurality of amplifier components; wherein the voltage level of said feedback loop substantially follows a voltage received at one of said plurality of said input signal receiving components; and an output component coupled with said feedback loop for providing an output signal corresponding to said voltage level of said feedback loop.

12. The circuit of claim 11, further comprising an output buffer interposed between said feedback loop and said output component.

13. The circuit of claim 11, wherein said individual sensors are an array of thermocouple sensors.

14. The circuit of claim 11, wherein said individual sensors are an array of thermistor sensors.

15. The circuit of claim 11, further comprising a plurality of signal buffers interposed between the input signal receiving component and the plurality of amplifier components, wherein each signal buffer component is coupled with the first input of a respective one of the amplifier components.

16. The circuit of claim 11, wherein the circuit further comprises a plurality of output leads coupled with the signal receiving component, the plurality of output leads providing each of the plurality of input signals to an electrocardiograph.

17. The circuit of claim 11, wherein the voltage received at said one of said plurality of said input receiving components corresponds to a high temperature measurement of the plurality of temperature measurements represented by the plurality of input signals.

18. The circuit of claim 11, wherein the voltage received at said one of said plurality of said input receiving components corresponds to a low temperature measurement of the plurality of temperature measurements represented by the plurality of input signals.

19. The circuit of claim 11, wherein any output across each of the rectifier components and a voltage Vee on each of the amplifier components combine to set a voltage on the feedback loop.

20. The circuit of claim 19, wherein the voltage on the feedback loop is an input voltage for inverting inputs on each of the amplifier components.

* * * * *